(12) United States Patent
Totsingan et al.

(10) Patent No.: US 9,102,712 B2
(45) Date of Patent: Aug. 11, 2015

(54) DENDRIMERIC PEPTIDES, PHARMACEUTICAL COMPOSITIONS AND METHODS OF USING THE SAME

(75) Inventors: Filbert Totsingan, Brooklyn, NY (US); Neville Robert Kallenbach, Philadelphia, PA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/818,876

(22) PCT Filed: Aug. 26, 2011

(86) PCT No.: PCT/US2011/001514
§ 371 (c)(1),
(2), (4) Date: May 6, 2013

(87) PCT Pub. No.: WO2012/026988
PCT Pub. Date: Mar. 1, 2012

(65) Prior Publication Data
US 2013/0210706 A1 Aug. 15, 2013

Related U.S. Application Data

(60) Provisional application No. 61/377,598, filed on Aug. 27, 2010.

(51) Int. Cl.
| | | |
|---|---|---|
| C07K 19/00 | (2006.01) | |
| C07K 7/02 | (2006.01) | |
| A61K 38/00 | (2006.01) | |
| C07K 14/00 | (2006.01) | |

(52) U.S. Cl.
CPC . *C07K 19/00* (2013.01); *C07K 7/02* (2013.01); *C07K 14/001* (2013.01); *A61K 38/00* (2013.01)

(58) Field of Classification Search
CPC ...... A61K 38/00; C07K 14/001; C07K 19/00; C07K 7/02
USPC .................................. 514/2.3; 530/327, 328
See application file for complete search history.

(56) References Cited

U.S. PATENT DOCUMENTS

| | | | |
|---|---|---|---|
| 3,679,653 | A | 7/1972 | Schuck |
| 5,229,490 | A | 7/1993 | Tam |
| 6,063,819 | A | 5/2000 | Marangos et al. |
| 7,056,942 | B2 * | 6/2006 | Hildesheim et al. .......... 514/411 |
| 2007/0053934 | A1 | 3/2007 | Kallenbach et al. |
| 2008/0312159 | A1 | 12/2008 | Kallenbach et al. |
| 2010/0093973 | A1 | 4/2010 | Nakagawa et al. |

FOREIGN PATENT DOCUMENTS

| | | |
|---|---|---|
| WO | 9836743 | 8/1998 |
| WO | 2007045010 | 4/2007 |
| WO | 2009025691 | 2/2009 |

OTHER PUBLICATIONS

Different diseases caused by microorganisms from Merck manual, p. 1. Accessed Sep. 18, 2014.*
Overview of Inflammatory Bowel Disease from Merck Manual, pp. 1-5. Accessed Sep. 18, 2014.*
Bacterial Urinary Tract Infections from Merck Manual, pp. 1-9. Accessed Sep. 18, 2014.*
Cellulitis from Merck Manual, pp. 1-3. Accessed Sep. 18, 2014.*
Cystic Fibrosis from Merck Manual, pp. 1-8. Accessed Sep. 18, 2014.*
Definition of isomers from http://www.answers.com/topic/isomer, pp. 1-10. Accessed Jul. 29, 2009.*
Hensley Scott, "Zyrtec Looks in Mirror and sees Xyzal from " http://blogs.wsj.com/health/2007/05/29/zyrtec-looks-in-mirror-and-sees-xyzal/, pp. 1-3. Accessed Jul. 29, 2009.*
Moore Daniel, "Xyzal: State of the Art Antihistamine," from http://allergies.about.com/b/2007/10/09/xyzal-state-of-the-art-antihistamine.htm, p. 1. Accessed Jul. 29, 2009.*
Thalidomide D or L safe, from www.skingenious.com/faq.html, pp. 1-7. Accessed Jul. 29, 2009.*
Tautomer from http://medical-dictionary.thefreedictionary.com/tautomer, pp. 1-2. Accessed Jul. 22, 2009.*
Han Hyo-Kyung, "Targeted Prodrug Design to Optimize Drug Delivery," AAPS Pharmsci 2000, 2(1): 1-11.*
Vippagunta SR, et al., Adv. Drug Delivery Rev. (2001) 48: 3-26.*
Van Baal et al., "Multivalent peptide and protein dendrimers using native chemical ligation," Angew. Chem. Int. Ed., 2005, 44: 5052-5057.*
Hancock et al., "The role of cationic antimicrobial peptides in innate host defenses", Trends in Microbiology, 2000, 8, 402-410.
Hancock et al., "Peptide antibiotics", Antimicrob Agents Chemother, 1999, 43, 1317-1323.

(Continued)

*Primary Examiner* — Julie Ha
(74) *Attorney, Agent, or Firm* — Klauber & Jackson LLC

(57) ABSTRACT

Novel peptide compounds and pharmaceutical compositions thereof are disclosed that have a formula represented by the following formula (I) wherein $L^1$, $L^2$, $L^3$, $Z$, $R^1$, $R^2$, $R^4$ and $R^5$ are as described herein. The compounds demonstrate antimicrobial activity and may be prepared as pharmaceutical compositions and used for the prevention and treatment of a variety of conditions in mammals including humans where microbial invasion is involved. The present peptides are particularly valuable as their effect is rapid, broad in spectrum and mostly indifferent to resistance provided by standard antibiotics.

16 Claims, No Drawings

(56) References Cited

OTHER PUBLICATIONS

Lehrer et al., "Antimicrobial peptides in mammalian and insect host defence", Curr Opin Immunol, 1999, 11, 23-27.

Sieprawska-Lupa et al., "Degradation of human antimicrobial peptide LL-37 by Staphylococcus aureus-derived proteinases", Antimicrobial Agents and Chemotherapy, 2004, 48, 4673-4679.

Van 't Hof et al., "Antimicrobial peptides: properties and applicability", Biological Chemistry, 2001, 382, 597-619.

Boman et al., "Antibacterial peptides: basic facts and emerging concepts", J Intern Med, 2003, 254, 197-215.

Tang et al., "Isolation, characterization, cDNA cloning, and antimicrobial properties of two distinct subfamilies of a-defensins fron rhesus macaque leukocytes", Infection and Immunity, 1999, 67, 6139-6144.

Fischetti et al., "Novel method to control pathogenic bacteria on human mucous membranes", 2003, Ann NY Acad Sci, 987, 207-214.

Zasloff, "Antimicrobial peptides of multicellular organisms", Nature, 2002, 415, 389-395.

Shai, "Mode of action of membrane active antimicrobial peptides", Biopolymers, 2002, 66, 236-248.

Tam et al., "Antimicrobial dendrimeric peptides", 2002, Eur J Biochem, 269, 923-932.

Dathe et al., "Cyclization increases the antimicrobial activity and selectivity of arginine- and tryptophan-containing hexapeptides", 2004, Biochemistry, 43, 9140-9150.

Epand et al., "Direct comparison of membrane interactions of model peptides composed of only Leu and Lys residues", Biopolymers, 2003, 71, 2-16.

Staubitz et al., "Structure-function relationships in the tryptophan-rich, antimicrobial peptide indolicidin", 2001, J Pept Sci, 7, 552-564.

Rennie et al., "Simple oligomers as antimicrobial peptide mimics", J Industrial Microbiology & Biotech, 2005, 32, 296-300.

Liu et al., "Length effects in antimicrobial peptides of the (RW)n. series", Antimicrobial Agents and Chemotherapy, 2007, 51, 597-603.

Zhou et al., "Synthesis and biological evaluation of novel 1,3,5-triazine derivatives as peptide mimetic antimicrobial agents", Bioorganic & Medicinal Chemistry Letters, 2008, 18, 1308-1311.

Tam et al., "Correlations of cationic charges with salt sensititivty and microbial specificity of cystine-stabilized B-strand antimicrobial peptides, The Journal of Biological Chemistry", 2002, 277, 50450-50456.

Tew et al., "De novo design of antimicrobial polymers, foldamers, and small molecules: from discovery to practical applications", Acc Chem Res., 2010, 43, 30-39.

Janiszewska et al., "Low molecular mass peptide dendrimers that express antimicrobial properties", Bioorg Med Chem Lett, 2003, 13, 3711-3713.

Tam et al., "Design of salt-insensitive glycine-rich antimicrobial peptides with cyclic tricystine structures", Biochemistry, 2000, 39, 715-7169.

Dempsey et al., "Enhanced membrane permeabilization and antibacterial activity of a disulfide-dimerized magainin analogue", Biochemistry, 2003, 42, 402-409.

Papo et al., "Effect of drastic sequence alteration and D-amino acid incorporation on the menmbrane binding behavior of lytic peptides", Biochemistry, 2004, 43, 6393-6403.

Xing et al., "Multivalent antibiotics via metal complexes: potent divalent vancomycins against vancomycin-resistant enteroccocci", J Med Chem, 2003, 46, 4904-4909.

Hou et al., "Antimicrobial dendrimer active against *Escherichia coli* biofilms", Bioorganic & Medicinal Chemistry Letters, 2009, 19, 5478-5481.

Liu et al., "Tuning the membrane selectivity of antimicrobial peptides by using multivalent design", ChemBioChem, 2007, 8, 2063-2065.

Polcyn et al., "Design of antimicrobially active small amphiphilic peptide dendrimers", Molecules, 2009, 14, 3881-3905.

\* cited by examiner

DENDRIMERIC PEPTIDES, PHARMACEUTICAL COMPOSITIONS AND METHODS OF USING THE SAME

GOVERNMENT SUPPORT

This invention was made at least in part, with government support under Grant No. N00014-03-1-0129 awarded by the Office of Naval Research. Accordingly, the United States Government has certain rights in the invention.

CROSS REFERENCE TO RELATED APPLICATIONS

The present application is a National Stage Application claiming the priority of PCT Application No. PCT/US2011/001514, filed Aug. 26, 2011, which in turn claims priority from U.S. Provisional Application No. 61/377,598, filed Aug. 27, 2010. Applicants claim the benefits of 35 U.S.C. §120 as to the PCT application and priority under 35 U.S.C. §119 as to the said U.S. Provisional application, and the entire disclosures of both applications are incorporated herein by reference in their entireties.

FIELD OF THE INVENTION

This invention relates to novel compositions and pharmaceutical compositions containing active peptides, and particularly, such peptides as demonstrate antimicrobial, antifungal or antiviral activity. The invention also relates to methods for the preparation of the peptide compositions, and their use in preventing and/or treating conditions resulting from the unwanted presence of microbial, fungal or viral activity. The invention generally relates to use of peptides and compositions thereof in pharmaceutical, healthcare, medical device, industrial, food, agricultural, and personal care applications.

BACKGROUND OF THE INVENTION

For the last few decades it has been known that a wide range of antimicrobial peptides are secreted by all manner of multicellular organisms in response to infection by foreign viruses, bacteria or fungi. Current research focuses on the mechanism by which the peptides kill, and synthetic design strategies which can enhance the activity of the peptides to a useful therapeutic level.

A wide range of antimicrobial peptides is secreted in plants and animals to challenge attack by foreign viruses, bacteria or fungi (Boman, 2003). These form part of the innate immune in response to infection, which is short term and fast acting relative to humoral immunity (Medzhitov, 2000). These cationic antimicrobial peptides have been considered as prospective antibiotics agents because their effect is rapid, broad spectrum and indifferent to resistance to standard antibiotics such as penicillins (Fischetti, 2003; Hancock, 1999). However, their success thus far has been limited, and is believed to be due to the requirement that they be present in a fairly high concentration to achieve killing (Hancock, 2000, Proc Natl Acad Sci), which is believed to exert a potentially cytotoxic effect on human erythrocytes as well as other cells and tissues. For these reasons current applications of these peptides are mostly topical.

Hundreds of such antimicrobial peptides have been studied extensively in order to understand the relationship between the structural features of the peptides and their antimicrobial activity, for the purpose of designing a new generation of antibiotics. Such known antimicrobial peptides are listed in The Antimicrobial Peptide Database, accessible via the University of Nebraska Medical Center website, the content and disclosure of which is incorporated herein by reference in its entirety. Representative peptides listed at the site are set forth hereinbelow by way of illustration and not limitation. Known antimicrobial peptides differ strikingly in size, sequence and structure, sharing only amphipathicity and positive charge (Hancock, 1999; Zasloff, 2002). While the external cell wall may be the initial target, several lines of evidence suggest that antimicrobial peptides act by lysing bacterial membranes. Cells become permeable following exposure to antimicrobial peptides, and their membrane potential is correspondingly reduced. While the actual target and mode of action of antimicrobial peptides are incompletely understood, proposed models emphasize the need to coat or cover a significant part of the membrane in order to produce a lethal effect. In "barrel-stave" models, several peptide monomers need to bind before formation of an aggregate that inserts itself into the bilayer to form a transmembrane pore. (Ehrenstein, 1977). In a somewhat different view, known as the "carpet model," peptide monomers must coat the target membrane surface extensively before sections of the membrane split off as vesicles, thereby destroying the integrity of the membrane (Shai, 2001). Both mechanisms account for the observed threshold concentration required for peptides to achieve lethality differently. In many cases this threshold is close to that for inflicting damage on host cells or tissues, as detected by hemolysis assays for example. Thus peptides have not found wide applications except as topical agents.

Several strategies have been pursued in efforts to increase the effectiveness of antimicrobial peptides (Tam, 2002; Janiszewska, 2003; Tam, 2000; Dathe, 2004; Tang, 1999; Dempsey, 2003; Epand, 2004; Papo, 2004). Sequence changes in natural peptides can notably reduce hemolysis while preserving activity (Staubitz, J. Pept. Sci. 2001, 7:552-564). Inserting unnatural D-amino acids or beta-amino acids into peptide sequences, combinatorial designs based on linear or cyclic sequences (Houghton, Ghadiri), synthetic chemical mimetics (DeGrado, Tew), and multivalent dendrimeric constructs of short peptides (Janiszewska, 2003; Xing, 2003) are other alternatives. In some cases improved solubility, salt resistance, stability and toxicity have been reported, with some reduction in $IC_{50}$ (Tam, 2002). None of the above highlighted references are included in the reference list.

Accordingly, many different designs for therapeutics have been reported, seeking to develop or improve activity under physiological conditions, low toxicity and proteolytic stability. Among promising approaches, polyvalent or multivalent antimicrobial polymers offer promise for enhancing the efficacy of existing antimicrobial monomer peptides and minimizing the problems accompanying conventional antimicrobial peptides by reducing the toxicity of the residue, increasing their efficiency and selectivity, and prolonging the lifetime of the effect. Especially, these include their ability to amplify cationic charges and hydrophobic clusters as the number of monomers increases. (Tam, 2002). For example, the multivalency of peptides incorporated with fragments of known antibacterial peptides in dendrimers has appeared to demonstrate good activity in the design of membranolytic peptides for therapeutic applications (Tam, 2002).

In this connection, U.S. Pat. No. 5,229,490 to Tam discloses a particular polymeric construction formed by the binding of multiple antigens to a dendritic core or backbone, the objective of which is to potentiate the concentration of antigen within a more economical and efficient molecule. While this construction has demonstrated advantages, greater activity and corresponding stability of the construct is still an important objective that is not fulfilled therein.

U.S. Pat. No. 3,679,653 to Schuck et al. discloses the preparation and use of polymer-based protein complexes, and particularly, relates to the preparation of such complexes with hormones such as bovine growth hormone, insulin and the like. Schuck et al. however, prepare complexes with full length native hormones, and bind the native material to the polymer backbone for the purpose of improving the delivery and availability of such hormones. The inventors qualify that the level of activity of the resulting complexes are somewhat uncertain, and in any event, do not represent that any dramatic improvements in such activity are either anticipated or realized.

U.S. Pat. No. 6,063,819 and WO1998/036743 to Marangos et al. disclose peptides attached to tris(2-aminoethyl)amine and tris(3-aminopropyl)amine as neuroprotectants.

US application 2010/0093973 discloses poly(aminoacid) compounds as phosphorus absorption inhibitors.

WO2007/045010 discloses dendrimeric peptides as inhibitors of angiogenesis.

WO2009/025691 discloses dendrimeric peptides as antimicrobials.

US application publication 2007/0053934 discloses polypeptides as antimicrobials.

US application publication 2008/0312159 discloses polypeptides as antimicrobials.

Antimicrobial peptides (AMPS) have been proposed as prospective antibiotic agents because of their ability to rapidly inactivate a wide range of microorganisms including Gram-positive and negative bacteria, fungi and some viruses. In many cases they are indifferent to current multi-drug resistant strains (Hancock and Chapple 1999; Lehrer and Ganz 1999). From the above, it remains that a continuing need exists for the development of modalities that can deliver effective antibiotic peptides in a manner that confers both improved stability and economy of the therapeutic, but importantly, significantly improves the therapeutic efficacy and strength of the resultant molecule. It is toward the fulfillment of these and other related objectives that the present invention is directed.

SUMMARY OF THE INVENTION

It has now been found that antibiotic peptide molecules covalently bound thereto, may be prepared, that provide enhanced stability, such as resistance to enzymatic digestion, along with dramatically increased activity of the antibiotic. In this latter regard, increases in activity on the order of ten-fold or more, over the same peptides in conventional form, are attained. This finding leads to novel peptides having therapeutic value. It also leads to pharmaceutical compositions having the peptide of the present invention as an active ingredient and to their use to treat, prevent or ameliorate a range of conditions in mammals of various genesis or etiology, however, primarily caused by bacteria, viruses, or fungi.

More particularly, the present invention relates to a pharmaceutical composition for preventing, treating, ameliorating or managing a disease or condition caused by micro organisms; wherein the pharmaceutical composition comprises a peptide according to formula I or Ia:

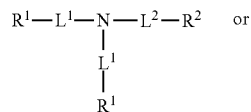

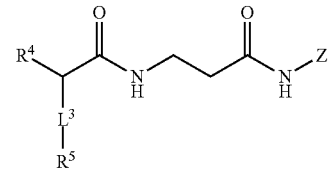

wherein
each $L^1$ and $L^3$ is independently substituted or unsubstituted $C_{2-5}$ alkylene;
$L^2$ is substituted or unsubstituted $C_{3-5}$ alkylene;
each $R^1$ is independently —NH-$(A)_m$-Z, or

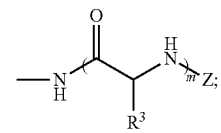

each A is independently an peptide residue selected from R, W, W*, F, Y, K, 2-Nal, Tta, and H*;
m is 1, 2, 3, or 4; each Z is independently H, Ac, or any other conventional N-protecting group;
$R^3$ is substituted or unsubstituted alkyl, aralkyl, heteroarylalkyl, aminoalkyl, or guanidinoalkyl;
$R^2$ is $R^1$; or $R^2$ is —N$(L^1$-$R^1)_2$;
$R^4$ is $R^5$, or

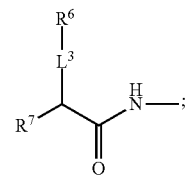

and each $R^5$, $R^6$, and $R^7$ is independently —NH—$(B')_n$—Z, or

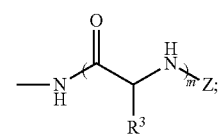

each B' is independently an peptide residue selected from R, W, W*, F, Y, K, 2-Nal, H*, and Tta;
n is 2, 3, or 4; each Z is independently H, Ac, or any other conventional N-protecting group; and
Tta is 2,5,7-trialkyltryptophan residue;
or a pharmaceutically acceptable salt, solvate or prodrug thereof; and stereoisomers, isotopic variants and tautomers thereof.

In another aspect, the invention provides a composition of a peptide according to formula I:

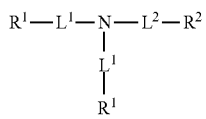

wherein
each $L^1$ is independently substituted or unsubstituted $C_{2-5}$ alkylene;
$L^2$ is substituted or unsubstituted $C_{3-5}$ alkylene;
each $R^1$ is independently —NH-$(A)_m$-Z;
each A is independently an peptide residue selected from R, W, W*, F, Y, K, 2-Nal, Tta, and H*;
m is 1, 2, 3, or 4; each Z is independently H, Ac, or any other conventional N-protecting group;
and
$R^2$ is $R^1$;
or a pharmaceutically acceptable salt, solvate or prodrug thereof; and stereoisomers, isotopic variants and tautomers thereof;
provided that when each $L^1$ and $L^2$ is —CH$_2$—CH$_2$—, then $R^1$ is other than —NH—RR—H.

In another aspect, the invention provides a composition of a peptide according to formula Ia:

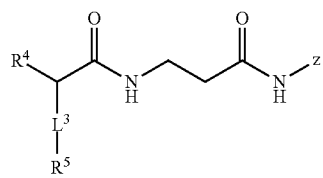

wherein
each $L^3$ is independently substituted or unsubstituted $C_{2-5}$ alkylene;
$R^3$ is substituted or unsubstituted alkyl, aralkyl, heteroarylalkyl, aminoalkyl, or guanidinoalkyl;
$R^4$ is $R^5$, or

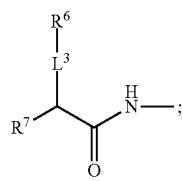

and each $R^5$, $R^6$, and $R^7$ is independently —NH—(B')$_n$—Z, or

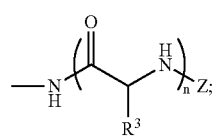

each B' is independently an peptide residue selected from R, W, W*, F, Y, K, 2-Nal, H*, and Tta;
n is 2, 3, or 4; each Z is independently H, Ac, or any other conventional N-protecting group; and Tta is 2,5,7-trialkyltryptophan residue;
or a pharmaceutically acceptable salt, solvate or prodrug thereof; and stereoisomers, isotopic variants and tautomers thereof;
provided that at least one of B's is Tta.

In one particular embodiment, with respect to peptides of formula Ma, Tta is Ttb residue.

In one particular embodiment, with respect to peptides of formula I, each $L^1$ is —CH$_2$—CH$_2$— or —CH$_2$—CH$_2$—CH$_2$—.

In a particular embodiment, with respect to peptides of formula I, $L^2$ is —CH$_2$—CH$_2$—CH$_2$—CH$_2$—.

In one particular embodiment, with respect to peptides of formula I, $R^2$ is $R^1$.

In another particular embodiment, with respect to peptides of formula I, $R^2$ is —N($L^1$-$R^1$)$_2$.

In one particular embodiment, with respect to peptides of formula I, the peptide is according to formula II:

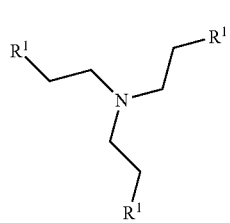

and each $R^1$ is as described for formula I.

In another particular embodiment, with respect to peptides of formula I, the peptide is according to formula IIIa or IIIb:

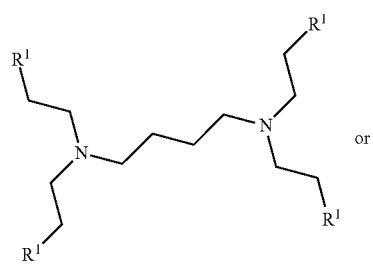

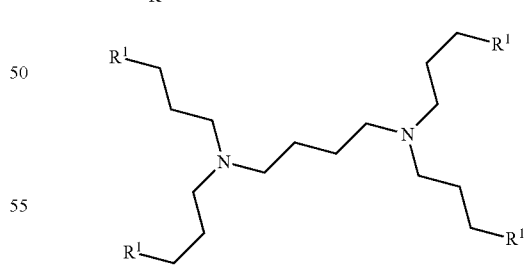

and each $R^1$ is as described for formula I.

In one particular embodiment, with respect to peptides of formula I-IIIb, each $R^1$ is —NH-$(A)_m$-Z; m is 1, 2 or 3; each A is independently R, W, K, F, Y, Tta, or H*; and Z is H or Ac. In a more particular embodiment, m is 2. In another particular embodiment, Z is H.

In another particular embodiment, with respect to peptides of formula I, the peptide is according to formula IV:

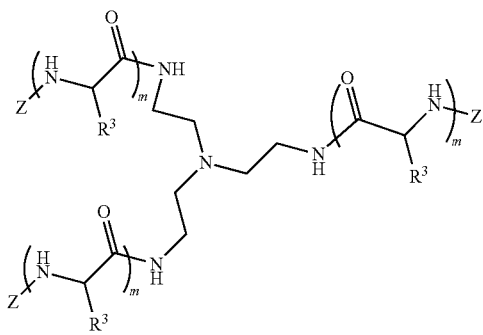

IV and wherein $R^3$, Z, and m are as described for formula I.

In a further particular embodiment, with respect to peptides of formula I, the peptide is according to formula Va or Vb:

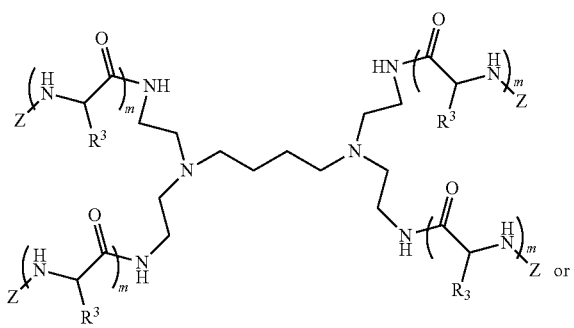

Va

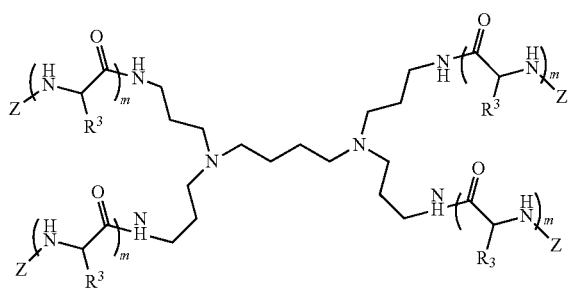

or

Vb and wherein $R^3$, Z, and m are as described for formula I.

In one embodiment, with respect to peptides of formula I-Vb, m is 1; $R^3$ is Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another aspect, the present invention provides compositions of peptides according to formula IIIa, IIIb, Va or Vb.

In a further aspect, the present invention provides a method for the preparation of the peptides of the invention.

In a further aspect, the peptides of the invention may be used to treat microbial or fungal conditions affecting lower animals, and possibly, plants. The peptides could be designed and assembled to include the peptides pertinent for the treatment of a particular microbe or fungus of interest, and then formulated into appropriate compositions and dosage forms for administration or application to an affected host. Moreover, such compositions may comprise the peptides of the invention in mixtures or combinations with other antibiotic agents, such as known antibiotic compounds. In such formulations, the peptides of the invention coact synergistically with the known antibiotic compounds, so that the resulting composition demonstrates improved effectiveness.

In a further aspect, the present invention provides pharmaceutical compositions comprising a peptide of the invention, and a pharmaceutical carrier, excipient or diluent. In this aspect of the invention, the pharmaceutical composition can comprise one or more variant peptides of the invention, prepared, for example, with a differing array of peptide linkers, to afford a more comprehensive treatment in the instance where a multiplicity of microbial/viral/fungal antigens are known to be present. Likewise, and as stated above, the pharmaceutical compositions may comprise one or more of the peptides of the invention, in combination with other antibiotic agents or compounds, including known antibiotic compounds.

In a further aspect of the invention, a method is disclosed for treating mammals, including humans, as well as lower mammalian species, susceptible to or afflicted with a condition attributable to or resulting from a microbial, viral or fungal infection, which method comprises administering an effective amount of a pharmaceutical composition containing or comprising the peptides just described.

In additional aspects, this invention provides methods for synthesizing the complexes of the invention, with representative synthetic protocols and pathways disclosed later on herein.

The present invention also encompasses antimicrobial compositions comprising any of the peptides of the invention, an antimicrobial substrate comprising any of the peptides of the invention, wherein such a peptide or peptides are bound to or incorporated into the substrate, and an article comprising an antimicrobial substrate. Such articles include, without limitation, a personal care item, an agricultural item, a cosmetic, a package, a food handling item, a food delivery item, a personal garment, a medical device, a personal hygiene item, an article intended for oral contact, a household item, a toy, or a liquid separation article.

Also encompassed herein are methods for making antimicrobial substrates using the peptides of the invention. The present invention further extends to the use of any of the peptides of the invention for the generation of antimicrobial substrates.

Other objects and advantages will become apparent to those skilled in the art from a consideration of the ensuing detailed description.

DETAILED DESCRIPTION OF THE INVENTION

Definitions

When describing the compounds, pharmaceutical compositions containing such compounds and methods of using such compounds and compositions, the following terms have the following meanings herein, unless otherwise indicated.

'Trp (W)' refers herein to an L-Tryptophan residue.
'Phe (F)' refers herein to an L-Phenylalanine residue.
'Lys (K)' refers herein to an L-Lysine residue.
'Arg (R)' refers herein to an L-Arginine residue.
'Tyr (Y)' refers herein to an L-Tyrosine residue.
'His (H*)' refers herein to a Histidine residue.
'(2Nal)' refers herein to 2-naphthyl)-L-alanine, and has a structure according to the following formula, when depicted as a residue:

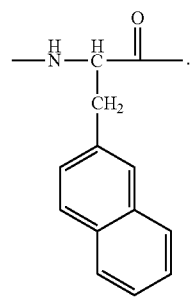 [SMILES: CNC(Cc1ccc2ccccc2c1)C(C)=O]

'(W*)' means 5-fluoro-DL-tryptophan, and has a structure according to the following formula, when depicted as a residue:

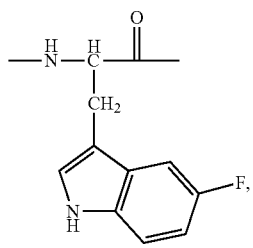 [SMILES: CNC(Cc1c[nH]c2ccc(F)cc12)C(C)=O]

'(Ttm)' means 2,5,7-trimethyl-DL-tryptophan, and has a structure according to the following formula, when depicted as a residue:

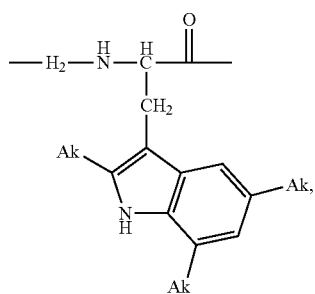

'(Tte)' means 2,5,7-triethyl-DL-tryptophan, and has a structure according to the following formula, when depicted as a residue:

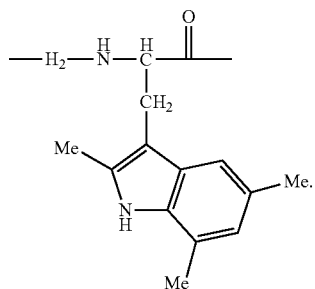

'(Ttip)' means 2,5,7-tri-iso-propyl-DL-tryptophan, and has a structure according to the following formula, when depicted as a residue:

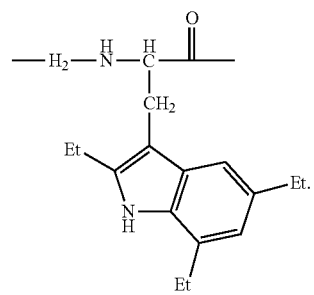

'(Ttb)' means 2,5,7-tri-t-butyl-DL-tryptophan, and has a structure according to the following formula, when depicted as a residue:

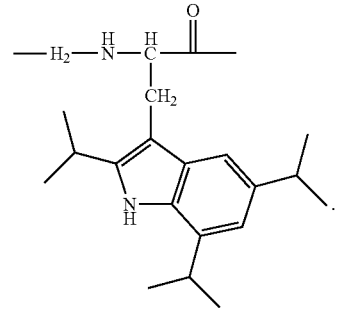

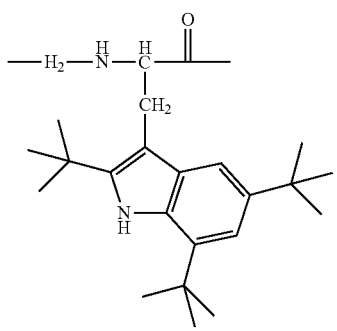

'Peptide' means a chain of amino acid residues having between 2 and about 100 amino acid residues, and includes peptides which are purified from naturally occurring products, or produced by synthetic or recombinant DNA methods, or that include one or more 'unnatural amino acids' as defined herein. Amino acid chains having greater than about 100 amino acid residues if present herein, are referred to as polypeptides.

The term 'residue' as used herein, refers to the monomeric form of an amino acid as it exists in a polymeric molecule. In this form, a hydrogen atom is displaced from the N-terminal end, and a hydroxyl group is displaced from the C-terminal end.

'Unnatural amino acids' means amino acids and corresponding peptides that are synthesized from single amino acid starting materials. Such unnatural amino acids may be prepared and used individually in accordance with the present invention, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989).

'Alkyl' means straight or branched aliphatic hydrocarbon having 1 to about 20 carbon atoms. Particular alkyl has 1 to about 12 carbon atoms. More particular is lower alkyl which has 1 to 6 carbon atoms. Most particular are groups such as methyl, ethyl and propyl. Branched means that one or more lower alkyl groups such as methyl, ethyl or propyl is attached to a linear alkyl chain. The term $C_1$-$C_6$ alkyl includes both branched and straight chain groups, exemplary straight chain groups include ethyl, propyl, butyl, exemplary branched chain groups include isopropyl, isoamyl, and the like.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 5 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Alkoxy' refers to the group —$OR^{24}$ where $R^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

'Substituted alkoxy' includes those groups recited in the definition of 'substituted' herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Aryloxy' refers to —O-aryl groups wherein 'aryl' is as defined above.

'Amino' refers to the radical —$NH_2$.

'Arylamino' means a radical —$NHR^{40}$ where $R^{40}$ represents an aryl group as defined herein.

'Substituted amino' refers to an amino group substituted with one or more of those groups recited in the definition of 'substituted' herein, and particularly refers to the group —$N(R^{36})_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —$N(R^{36})_2$ is an amino group. Exemplary 'substituted amino' groups are —$NR^{36}$—$C_1$-$C_8$ alkyl, —$NR^{36}$—$(CH_2)_t(C_6$-$C_{10}$ aryl), —$NR^{36}$—$(CH_2)_t(C_5$-$C_{10}$ heteroaryl), —$NR^{36}$—$(CH_2)_t(C_3$-$C_{10}$ cycloalkyl), and —$NR^{36}$—$(CH_2)_t$ ($C_5$-$C_{10}$ heterocycloalkyl), wherein t is an integer from 0 to 4, each $R^{36}$ independently represents H or $C_1$-$C_6$ alkyl and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Substituted' refers to a group in which one or more hydrogen atoms are each independently replaced with the same or different substituent(s). Typical substituents are selected from the group consisting of: —X, —$R^{46}$, —$O^-$, =O, —$OR^{46}$, —$SR^{46}$, —$S^-$, =S, —$NR^{46}R^{47}$, =$NR^{46}$, —$CX_3$, —$CF_3$, —CN, —OCN, —SCN, —NO, —$NO_2$, —$N_2$, —$N_3$, —$S(O)_2O^-$, —$S(O)_2OH$, —$S(O)_2R^{46}$, —$OS(O_2)O^-$, —OS$(O)_2R^{46}$, —$P(O)(O^-)_2$, —$P(O)(OR^{46})(O)$, —$OP(O)(OR^{46})(OR^{47})$, —$C(O)R^{46}$, —$C(S)R^{46}$, —$C(O)OR^{46}$, —$C(O)NR^{46}R^{47}$, —$C(O)O^-$, $C(S)OR^{46}$, —$NR^{48}C(O)NR^{46}R^{47}$, —$NR^{48}C(S)NR^{46}R^{47}$, $NR^{49}C(NR^{48})NR^{46}R^{47}$ and —$C(NR^{48})NR^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{50}R^{51}$, —$C(O)R^{50}$ or —$S(O)_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl. In a particular embodiment, substituted groups are substituted with one or more substituents, particularly with 1 to 3 substituents, in particular with one substituent group. In a further particular embodiment the substituent group or groups are selected from halo, cyano, nitro, trifluoromethyl, trifluoromethoxy, azido, —NR'''$SO_2$R'', —$SO_2$NR''R''', —C(O)R'', —C(O)OR'', —OC(O)R'', —NR'''C(O)R'', —C(O)NR''R''', —NR''R''', —(CR'''R''')$_m$OR''', wherein, each R is independently selected from H, $C_1$-$C_8$ alkyl, —$(CH_2)_t(C_6$-$C_{10}$ aryl), —$(CH_2)_t(C_5$-$C_{10}$ heteroaryl), —$(CH_2)_t(C_3$-$C_{10}$ cycloalkyl), and —$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy. Each R'' independently represents H or $C_1$-$C_6$alkyl.

'Pharmaceutically acceptable' means approved by a regulatory agency of the Federal or a state government or listed in the U.S. Pharmacopoeia or other generally recognized pharmacopoeia for use in animals, and more particularly in humans.

'Pharmaceutically acceptable vehicle' refers to a diluent, adjuvant, excipient or carrier with which a compound of the invention is administered.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

'Prodrugs' refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Solvate' refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

'Subject' includes humans. The terms 'human,' patiene and 'subject' are used interchangeably herein.

'Tautomers' refer to compounds that are interchangeable forms of a particular compound structure, and that vary in the displacement of hydrogen atoms and electrons. Thus, two structures may be in equilibrium through the movement of E electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term 'isotopic variant' refers to a compound that comprises an unnatural proportion of an isotope of one or more of the atoms that constitute such compound. For example, an 'isotopic variant' of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H$/D, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed 'isomers.' Isomers that differ in the arrangement of their atoms in space are termed 'stereoisomers.'

Stereoisomers that are not mirror images of one another are termed 'diastereomers' and those that are non-superimposable mirror images of each other are termed 'enantiomers.' When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture.'

The Peptides

As set forth earlier herein, the peptide dendrimer compounds comprise antimicrobial/antiviral/antifungal peptides. The compounds may be dipeptides and may have a lethal effect on bacteria, viruses or fungi. More particularly, the peptides may be any antimicrobial peptides, including natural products found in organisms, fragments of natural peptides, and any synthetic analogs or de novo designs. These peptides can accordingly include non-natural amino acids: beta-amino acids, d-amino acids and/or non-indigenous amino acids.

More particularly, the present invention relates to a pharmaceutical composition for preventing, treating, ameliorating or managing a disease or condition caused by micro organisms; wherein the pharmaceutical composition comprises a peptide according to formula I or Ia:

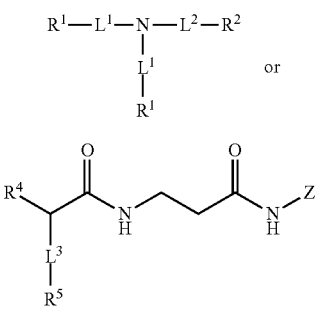

wherein
each $L^1$ and $L^3$ is independently substituted or unsubstituted $C_{2-5}$ alkylene;
$L^2$ is substituted or unsubstituted $C_{3-5}$ alkylene;
each $R^1$ is independently —NH-(A)$_m$-Z, or

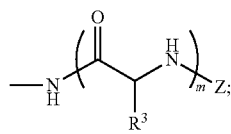

each A is independently an peptide residue selected from R, W, W*, F, Y, K, 2-Nal, Tta, and H*;
m is 1, 2, 3, or 4; each Z is independently H, Ac, or any other conventional N-protecting group;
$R^3$ is substituted or unsubstituted alkyl, aralkyl, heteroarylalkyl, aminoalkyl, or guanidinoalkyl;
$R^2$ is $R^1$; or $R^2$ is —N($L^1$-$R^1$)$_2$;
$R^4$ is $R^5$, or

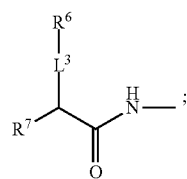

and each $R^5$, $R^6$, and $R^7$ is independently —NH—(B')$_n$—Z, or

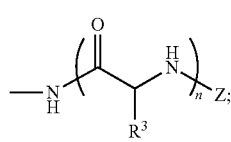

each B' is independently an peptide residue selected from R, W, W*, F, Y, K, 2-Nal, H*, and Tta;
n is 2, 3, or 4; each Z is independently H, Ac, or any other conventional N-protecting group; and
Tta is 2,5,7-trialkyltryptophan residue;
or a pharmaceutically acceptable salt, solvate or prodrug thereof; and stereoisomers, isotopic variants and tautomers thereof.
In another aspect, the invention provides a composition of a peptide according to formula Ia:

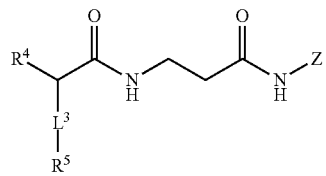

wherein
each $L^3$ is independently substituted or unsubstituted $C_{2-5}$ alkylene;
$R^3$ is substituted or unsubstituted alkyl, aralkyl, heteroarylalkyl, aminoalkyl, or guanidinoalkyl;
$R^4$ is $R^5$, or

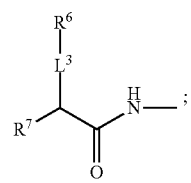

and each $R^5$, $R^6$, and $R^7$ is independently —NH—(B')$_n$—Z, or

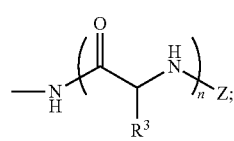

each B' is independently an peptide residue selected from R, W, W*, F, Y, K, 2-Nal, H*, and Tta;
n is 2, 3, or 4; each Z is independently H, Ac, or any other conventional N-protecting group; and
Tta is 2,5,7-trialkyltryptophan residue;
or a pharmaceutically acceptable salt, solvate or prodrug thereof; and stereoisomers, isotopic variants and tautomers thereof;
provided that at least one of B's is Tta.
In one particular embodiment, with respect to peptides of formula I-Ia, Tta is Ttb
In a further aspect, the invention provides a composition of a peptide according to formula I:

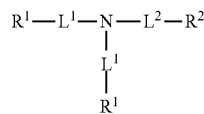

wherein
each $L^1$ is independently substituted or unsubstituted $C_{2-5}$ alkylene;
$L^2$ is substituted or unsubstituted $C_{3-5}$ alkylene;
each $R^1$ is independently —NH-(A)$_m$-Z;
each A is independently an peptide residue selected from R, W, W*, F, Y, K, 2-Nal, Tta, and H*;
m is 1, 2, 3, or 4; each Z is independently H, Ac, or any other conventional N-protecting group;

and

R² is R¹;

or a pharmaceutically acceptable salt, solvate or prodrug thereof; and stereoisomers, isotopic variants and tautomers thereof;

provided that when each L¹ and L² is —CH₂—CH₂—, then R¹ is other than —NH—RR—H.

In one embodiment, with respect to peptides of formula I-Ia, each L¹ and L³ is independently selected from —CH₂—CH₂—, —CH₂—CH₂—CH₂—, and —CH₂—CH₂—CH₂—CH₂—. In one particular embodiment, each L¹ is —CH₂—CH₂— or —CH₂—CH₂—CH₂—. In a more particular embodiment, each L¹ is —CH₂—CH₂—.

In one embodiment, with respect to peptides of formula I, L² is selected from —CH₂—CH₂—CH₂—, —CH₂—CH₂—CH₂—CH₂—, and —CH₂—CH₂—CH₂—CH₂—CH₂—.

In a particular embodiment, with respect to peptides of formula I, L² is —CH₂—CH₂—CH₂—CH₂—.

In a particular embodiment, with respect to peptides of formula Ia, L³ is —CH₂—CH₂—CH₂—CH₂—.

In one embodiment, with respect to peptides of formula I, R² is R¹.

In one embodiment, with respect to peptides of formula I, the peptide is according to formula II:

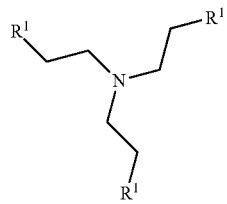

II and each R¹ is as described for formula I.

In another embodiment, with respect to peptides of formula I, R² is —N(L¹-R¹)₂.

In one particular embodiment, with respect to peptides of formula I, the peptide is according to formula IIIa or IIIb:

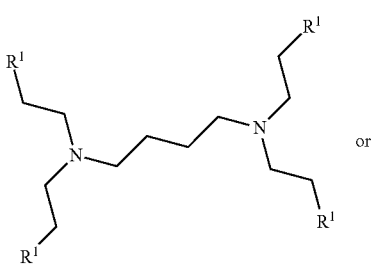

IIIa or

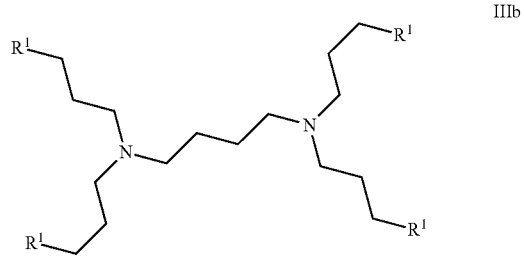

IIIb and each R¹ is as described for formula I.

In one embodiment, with respect to peptides of formula I-IIIb, each R¹ is —NH-(A)ₘ-Z; and each A, m and Z are as described for formula I.

In another embodiment, with respect to peptides of formula I-IIIb, each R¹ is —NH-(A)ₘ-Z; m is 1; A is R, W, K, F, Y, Tta, or H*; and Z is H or Ac.

In another embodiment, with respect to peptides of formula I-IIIb, each R¹ is —NH-(A)ₘ-Z; m is 2; each A is independently R, W, K, F, Y, Tta, or H*; and Z is H or Ac.

In another embodiment, with respect to peptides of formula I-IIIb, each R¹ is —NH-(A)ₘ-Z; m is 3; each A is independently R, W, K, F, Y, Tta, or H*; and Z is H or Ac.

In another embodiment, with respect to peptides of formula I-IIIb, each R¹ is independently —NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, or —NH—FK—Z; and Z is H or Ac. In one embodiment, any one of the amino acid residues is replaced with Tta. In one particular embodiment, any one of the amino acid residues is replaced with Ttm, Tte, Ttip, or Ttb.

In another embodiment, with respect to peptides of formula I-IIIb, each R¹ is independently —NH—RWW—Z, —NH—RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z; and Z is H or Ac. In one embodiment, any one of the amino acid residues is replaced with Tta. In one particular embodiment, any one of the amino acid residues is replaced with Ttm, Tte, Ttip, or Ttb.

In one particular embodiment, with respect to peptides of formula I-IIIb, Z is H.

In another particular embodiment, with respect to peptides of formula I, the peptide is according to formula IV:

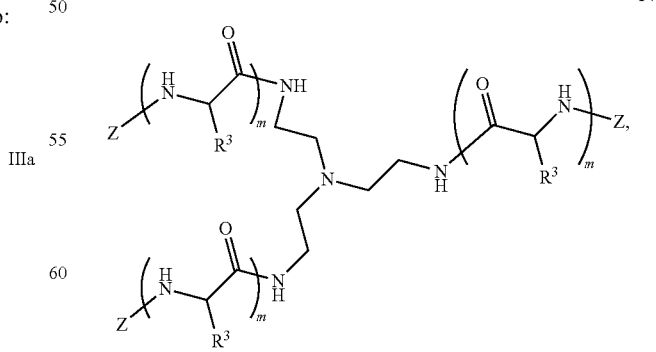

IV and wherein R³, Z, and m are as described for formula I.

In a further particular embodiment, with respect to peptides of formula I, the peptide is according to formula Va or Vb:

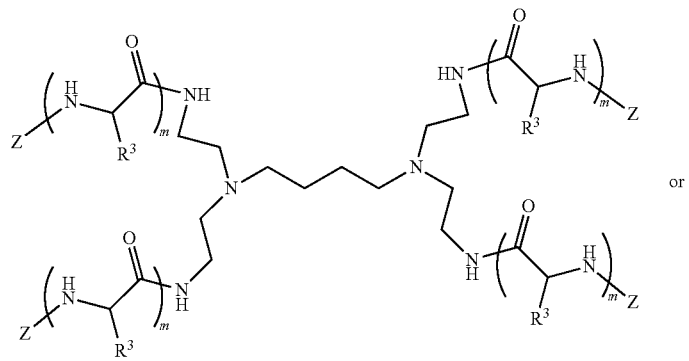

Va

or

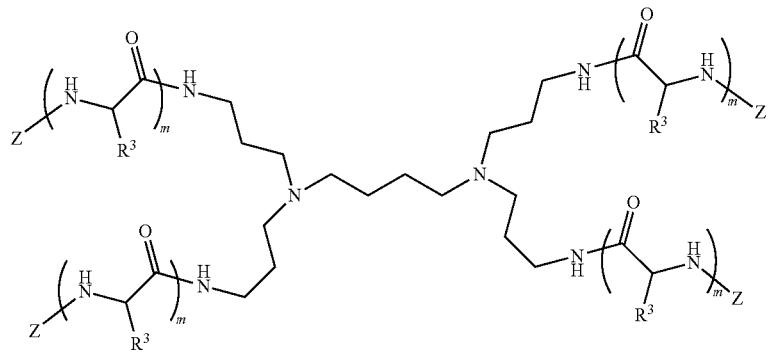

Vb and wherein R³, Z, and m are as described for formula I.

In one embodiment, with respect to peptides of formula I-Vb, m is 1; R³ is Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another embodiment, with respect to peptides of formula I-Vb, m is 2; each R³ is independently Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another embodiment, with respect to peptides of formula I-Vb, m is 3; each R³ is independently Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another embodiment, with respect to peptides of formula I-Vb, each R³ is benzyl, (4-hydroxy)phenylmethyl, 4-aminobutyl, 5-guanadinopentyl, imidazomethyl, or indolylmethyl.

In yet another aspect, the present invention provides a pharmaceutical composition for preventing, treating, ameliorating or managing a disease or condition caused by micro organisms; wherein the pharmaceutical composition comprises a peptide according to formula Ia:

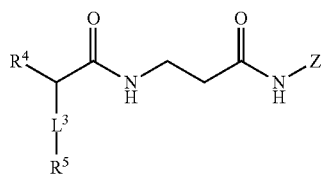

Ia wherein
each L³ is independently substituted or unsubstituted $C_{2-5}$ alkylene;

R³ is substituted or unsubstituted alkyl, aralkyl, heteroarylalkyl, aminoalkyl, or guanidinoalkyl;
R⁴ is R⁵, or

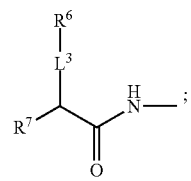

and each R⁵, R⁶, and R⁷ is independently —NH—(B')$_n$—Z, or

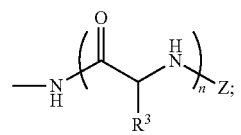

each B' is independently an peptide residue selected from R, W, W*, F, Y, K, 2-Nal, H*, and Tta;
n is 2, 3, or 4; each Z is independently H, Ac, or any other conventional N-protecting group; and
Tta is a 2,5,7-trialkyltryptophan residue;
or a pharmaceutically acceptable salt, solvate or prodrug thereof; and stereoisomers, isotopic variants and tautomers thereof;
provided that at least one of the B's is Tta.

In one embodiment, with respect to the pharmaceutical composition, the peptide is according to formula Ia, and L³ is —CH₂—CH₂—CH₂—CH₂—.

In one embodiment, with respect to the pharmaceutical composition, the peptide is according to formula VIa or VIb:

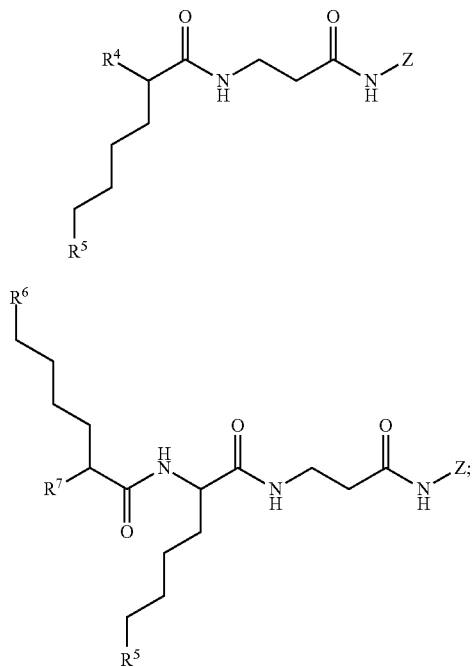

VIa

VIb wherein $R^4$ is $R^5$;
each $R^5$, $R^6$, and $R^7$ is independently —NH—(B')$_n$—Z,
each B' is independently an peptide residue selected from R, W, W*, F, Y, K, 2-Nal, H*, and Tta;
n is 2, 3, or 4; each Z is independently H, Ac, or any other conventional N-protecting group; and
Tta is 2,5,7-trialkyltryptophan residue;
or a pharmaceutically acceptable salt, solvate or prodrug thereof; and stereoisomers, isotopic variants and tautomers thereof;
provided that at least one of B's is Tta.

In one embodiment, with respect to the pharmaceutical composition, the peptide is according to formula Ia, and VIa-VIb, and n is 2, 3, or 4; and each B' is independently selected from R, W, W*, F, Y, K, 2-Nal, H*, and Tta.

In one embodiment, with respect to the pharmaceutical composition, the peptide is according to formula Ia, and VIa-VIb, and n is 2, 3, or 4; and each B' is independently selected from R, W, Ttm, Tte, Ttip, and Ttb; and wherein Ttm is a 2,5,7-trimethyltryptophan residue; Tte is a 2,5,7-triethyltryptophan residue; Ttip is a 2,5,7-tri-iso-propyl-tryptophan residue; and Ttb is a 2,5,7-tri-t-butyltryptophan residue.

In one embodiment, with respect to the pharmaceutical composition, the peptide is according to formula Ia, and VIa-VIb, and n is 2, 3, or 4; and each B' is independently selected from R, W, and Ttb.

In one embodiment, with respect to the pharmaceutical composition, the peptide is according to formula Ia, and VIa-VIb, and each $R^5$, $R^6$, and $R^7$ is independently selected from —NH—(RW)—Z, —NH—(RTtb)-Z, —NH—(WR)—Z, —NH—(WTtb)-Z, —NH-(TtbR)—Z, —NH-(TtbW)—Z, —NH—(RWR)—Z, —NH—(RTtbR)—Z, —NH—(WTtbR)—Z, —NH—(WTtbW)—Z, —NH—(RTtbW)—Z, —NH-(TtbRW)—Z, —NH-(TtbWR)—Z, —NH-(TtbRR)—Z, —NH—(TtbWW)—Z, —NH—(RTtbTtb)-Z, —NH—(WTtbTtb)-Z, —NH-(TtbTtbR)—Z, —NH-(TtbTtbW)—Z, —NH-(TtbRTtb)-Z, —NH-(TtbWTtb)-Z, and —NH-(TtbTtbTtb)-Z; and Z is H, or Ac;

provided that at least one of $R^4$ and $R^5$; and at least one of $R^5$, $R^6$, and $R^7$, contains Ttb residue.

In one embodiment, with respect to the pharmaceutical composition, the peptide is according to formula VIIa, VIIb, VIIc, VIId, VIIe, or VIIf:

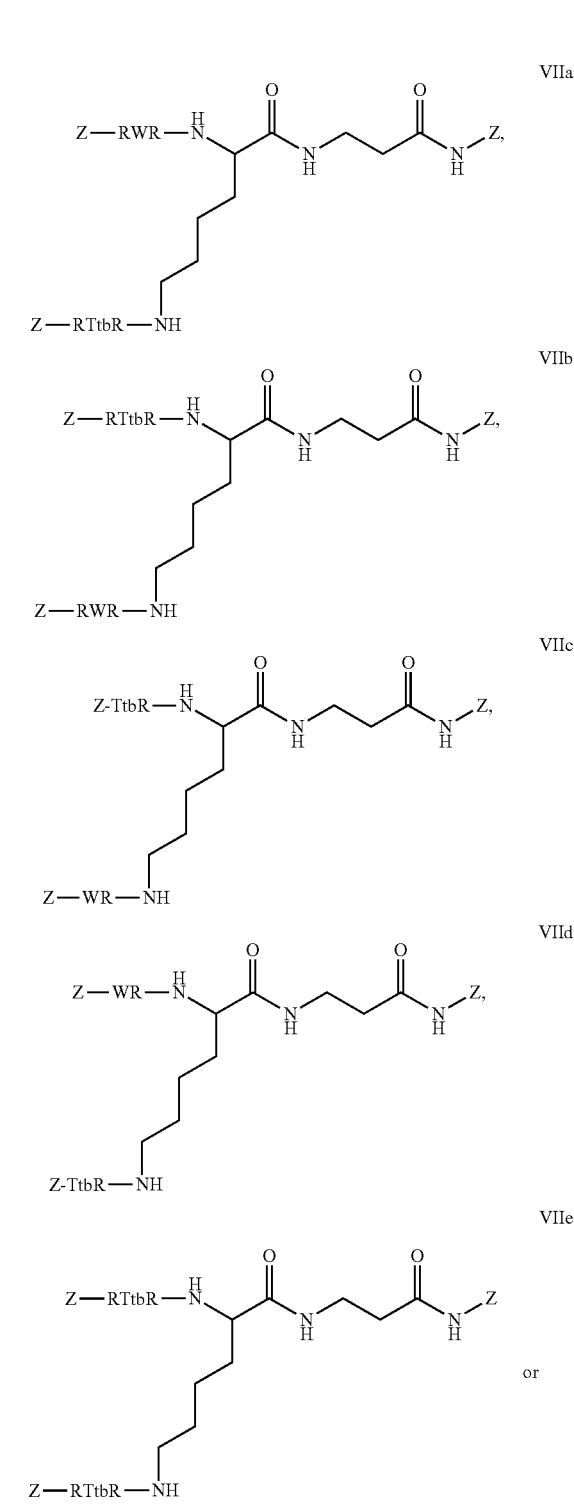

VIIa

VIIb

VIIc

VIId

VIIe or

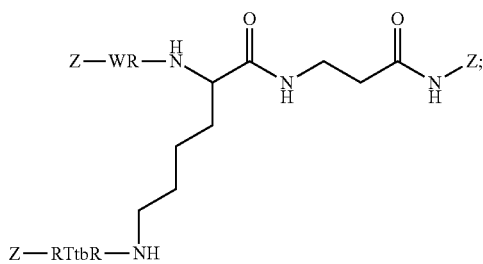
wherein each Z is independently H, or Ac.
In one embodiment, with respect to the pharmaceutical composition, the peptide is according to formula VIIIa, VIIIb, VIIIc, VIIId, VIIIe, or VIIIf:
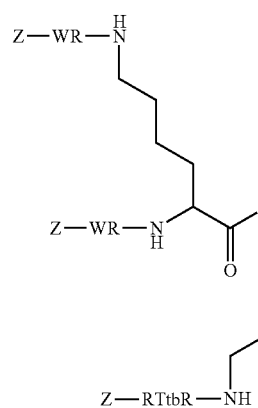
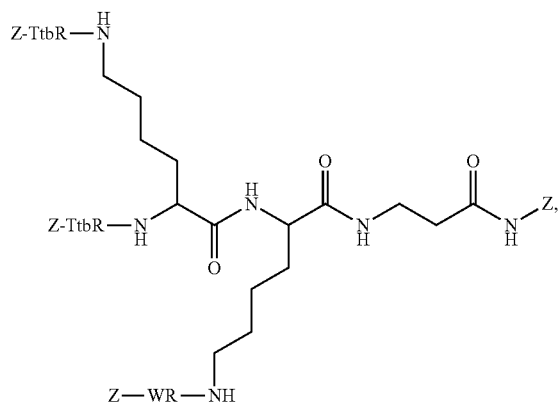
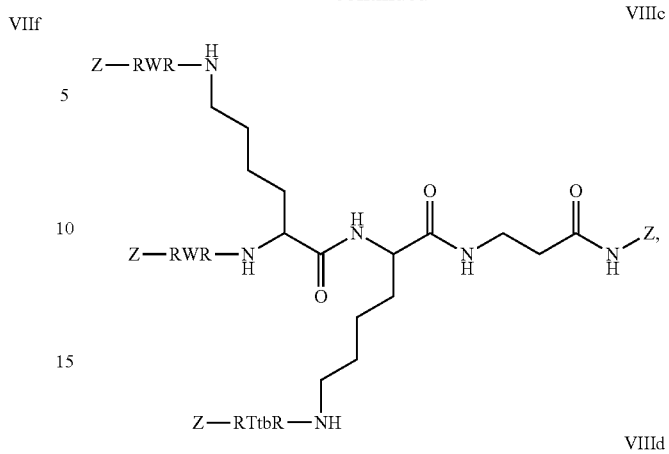
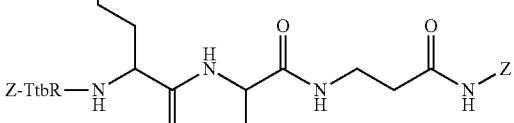
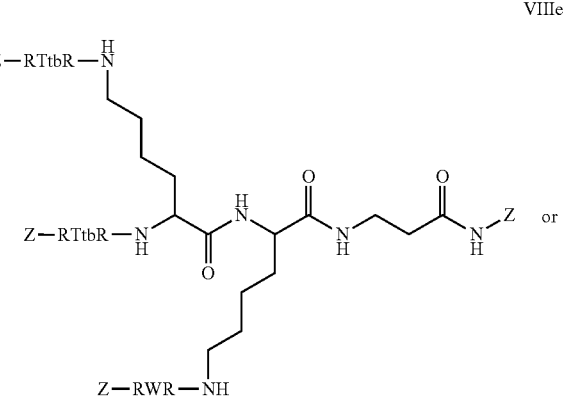
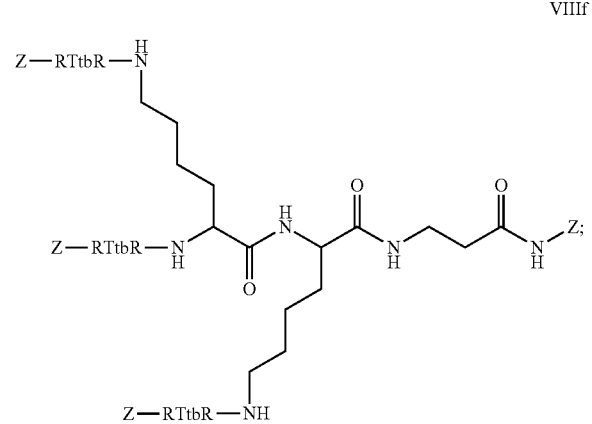

wherein each Z is independently H, or Ac.

In one embodiment, with respect to the pharmaceutical composition, the peptide is according to formula Ia, and VIa-VIIIf, and Z is H.

In one embodiment, with respect to the pharmaceutical composition, the peptide is according to formula Ia, and VIa-VIIIf, and Z is Ac.

An another aspect of the invention provides a composition of a peptide according to formula I:

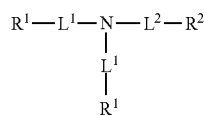

I wherein $L^1$, $L^2$ and $R^1$ are as described for formula I; and $R^2$ is —N($L^1$-$R^1$)$_2$;

or a pharmaceutically acceptable, salt, solvate or prodrug thereof; and stereoisomers, isotopic variants and tautomers thereof.

In one embodiment, with respect to the composition of peptides of formula I, each $L^1$ is selected from —CH$_2$—CH$_2$—, —CH$_2$—CH$_2$—CH$_2$—, and —CH$_2$—CH$_2$—CH$_2$—CH$_2$—.

In another embodiment, with respect to the composition of peptides of formula I, each $L^1$ is —CH$_2$—CH$_2$—.

In another embodiment, with respect to the composition of peptides of formula I, $L^2$ is selected from —CH$_2$—CH$_2$—CH$_2$—, —CH$_2$—CH$_2$—CH$_2$—CH$_2$—, and —CH$_2$—CH$_2$—CH$_2$—CH$_2$—CH$_2$—.

In one particular embodiment, with respect to the composition of peptides of formula I, $L^2$ is —CH$_2$—CH$_2$—CH$_2$—CH$_2$—.

In one embodiment, with respect to the composition of peptides of formula I, the peptide is according to formula IIIa or IIIb:

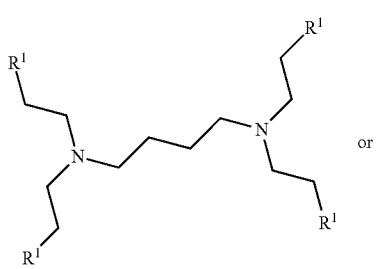

IIIa or

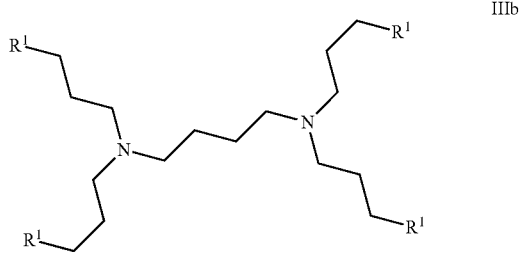

IIIb and each $R^1$ is as described for formula I.

In one embodiment, with respect to the composition of peptides of formulae I, IIIa-IIIb, each $R^1$ is —NH-(A)$_m$-Z; and each A, m and Z are as described for formula I.

In another embodiment, with respect to the composition of peptides of formulae I, IIIa-IIIb, each $R^1$ is —NH-(A)$_m$-Z; m is 1; A is R, W, K, F, Y, Tta, or H*; and Z is H or Ac.

In another embodiment, with respect to the composition of peptides of formulae I, IIIa-IIIb, each $R^1$ is —NH-(A)$_m$-Z; m is 2; each A is independently R, W, K, F, Y, Tta, or H*; and Z is H or Ac.

In another embodiment, with respect to the composition of peptides of formulae I, IIIa-IIIb, each $R^1$ is —NH-(A)$_m$-Z; m is 3; each A is independently R, W, K, F, Y, Tta, or H*; and Z is H or Ac.

In another embodiment, with respect to the composition of peptides of formulae I, IIIa-IIIb, m is q; and A is selected from Tta.

In another embodiment, with respect to the composition of peptides of formulae I, IIIa-IIIb, m is 2, 3, or 4; and at least on of As is selected from Tta.

In another embodiment, with respect to the composition of peptides of formulae I, IIIa-IIIb, each $R^1$ is independently —NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, or —NH—FK—Z; and Z is H or Ac. In one embodiment, any one of the amino acid residues is replaced with Tta. In one particular embodiment, any one of the amino acid residues is replaced with Ttm, Tte, Ttip, or Ttb.

In another embodiment, with respect to the composition of peptides of formulae I, each $R^1$ is independently —NH—RWW—Z, RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z; and Z is H or Ac. In one embodiment, any one of the amino acid residues is replaced with Tta. In one particular embodiment, any one of the amino acid residues is replaced with Ttm, Tte, Ttip, or Ttb.

In another embodiment, with respect to the composition of peptides of formulae I, IIIa-IIIb, Z is H.

In another embodiment, with respect to the composition of peptides of formulae I, the peptide is according to formula Va or Vb:

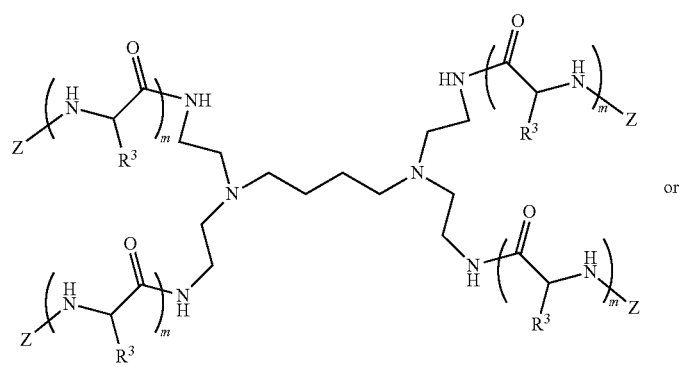

Va

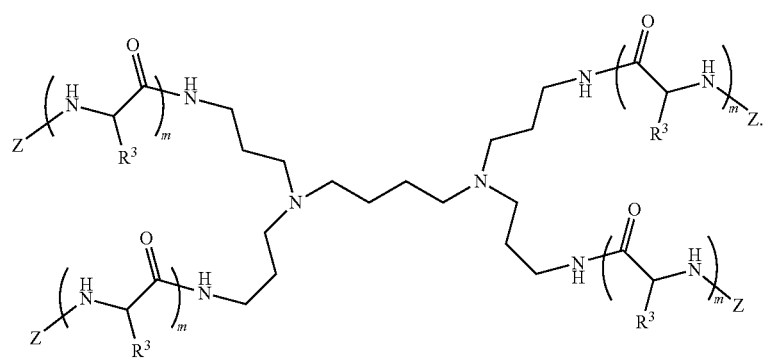

Vb and wherein $R^3$, Z, and m are as described for formula I.

In one embodiment, with respect to the composition of peptides of formulae I, IIIa-IIIb, and Va-Vb, m is 1; $R^3$ is Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another embodiment, with respect to the composition of peptides of formulae I, IIIa-IIIb, and Va-Vb, m is 2; each $R^3$ is independently Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another embodiment, with respect to the composition of peptides of formulae I, IIIa-IIIb, and Va-Vb, m is 3; each $R^3$ is independently Me, i-Pr, i-Bu, sec-Bu, benzyl, (4-hydroxy)phenylmethyl, 4-aminobutyl, 5-guanadinopentyl, imidazomethyl, or indolylmethyl; and Z is H or Ac.

In another embodiment, with respect to the composition of peptides of formulae I, IIIa-IIIb, and Va-Vb, each $R^3$ is benzyl, (4-hydroxy)phenylmethyl, 4-aminobutyl, 5-guanadinopentyl, imidazomethyl, or indolylmethyl.

In one particular embodiment, with respect to the pharmaceutical composition of peptides of formula I, the peptide is N[—CH$_2$—CH$_2$—W—H]$_3$, N[—CH$_2$—CH$_2$—WR—H]$_3$, or N[—CH$_2$—CH$_2$—WK—H]$_3$.

In another embodiment, with respect to the composition or pharmaceutical composition of peptides of formula I, the peptide is

[H—RW—CH$_2$—CH$_2$—CH$_2$—]$_2$N—CH$_2$—CH$_2$—CH$_2$—CH$_2$—N[—CH$_2$—CH$_2$—CH$_2$—WR—H]$_2$.

In a further particular embodiment, with respect to the composition or pharmaceutical composition of peptides of formula I, the peptide is

[H—WK—CH$_2$—CH$_2$—CH$_2$-]$_2$N—CH$_2$—CH$_2$—CH$_2$—CH$_2$—N[—CH$_2$—CH$_2$—CH$_2$—WK—H]$_2$.

In certain aspects, the present invention provides a peptide according to formula Ia:

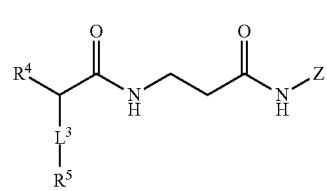

Ia wherein each $L^3$ is independently substituted or unsubstituted $C_{2-5}$ alkylene;

$R^3$ is substituted or unsubstituted alkyl, aralkyl, heteroarylalkyl, aminoalkyl, or guanidinoalkyl;

$R^4$ is $R^5$, or

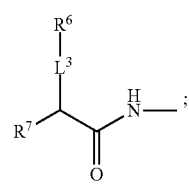

and each $R^5$, $R^6$, and $R^7$ is independently —NH—(B')$_n$—Z, or

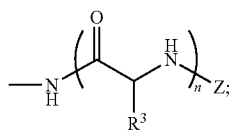

each B' is independently an peptide residue selected from R, W, W*, F, Y, K, 2-Nal, H*, and Tta;

n is 2, 3, or 4; each Z is independently H, Ac, or any other conventional N-protecting group; and Tta is 2,5,7-trialkyltryptophan residue;

or a pharmaceutically acceptable salt, solvate or prodrug thereof; and stereoisomers, isotopic variants and tautomers thereof;

provided that at least one of the B's is Tta.

In one embodiment, with respect to the peptide according to formula Ia, $L^3$ is —CH$_2$—CH$_2$—CH$_2$—CH$_2$—.

In one embodiment, with respect to the peptide according to formula Ia, the peptide is according to formula VIa or VIb:

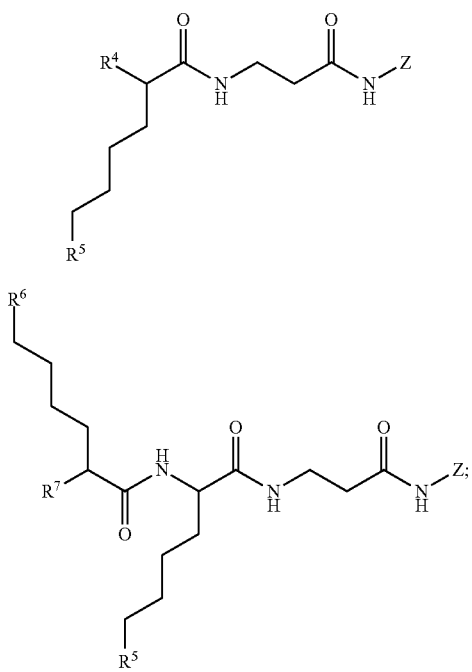

wherein $R^4$ is $R^5$;

each $R^5$, $R^6$, and $R^7$ is independently —NH—(B')$_n$—Z, each B' is independently an peptide residue selected from R, W, W*, F, Y, K, 2-Nal, H*, and Tta;

n is 2, 3, or 4; each Z is independently H, Ac, or any other conventional N-protecting group; and Tta is a 2,5,7-trialkyltryptophan residue;

or a pharmaceutically acceptable salt, solvate or prodrug thereof; and stereoisomers, isotopic variants and tautomers thereof;

provided that at least one of the B's is Tta.

In one embodiment, with respect to the peptide according to formula Ia, and VIa-VIb, n is 2, 3, or 4; and each B' is independently selected from R, W, W*, F, Y, K, 2-Nal, H*, and Tta.

In one embodiment, with respect to the peptide according to formula Ia, and VIa-VIb, n is 2, 3, or 4; and each B' is independently selected from R, W, Ttm, Tte, Ttip, and Ttb; and wherein Ttm is 2,5,7-trimethyltryptophan residue; Tte is 2,5,7-triethyltryptophan residue; Ttip is 2,5,7-tri-iso-propyl-tryptophan residue; and Ttb is 2,5,7-tri-t-butyltryptophan residue.

In one embodiment, with respect to the peptide according to formula Ia, and VIa-VIb, n is 2, 3, or 4; and each B' is independently selected from R, W, and Ttb.

In one embodiment, with respect to the peptide according to formula Ia, and VIa-VIb, each $R^5$, $R^6$, and $R^7$ is independently selected from —NH—(RW)—Z, —NH—(RTtb)-Z, —NH—(WR)—Z, —NH—(WTtb)-Z, —NH-(TtbR)—Z, —NH-(TtbW)—Z, —NH—(RWR)—Z, —NH—(RTtbR)—Z, —NH—(WTtbR)—Z, —NH—(WTtbW)—Z, —NH—(RTtbW)—Z, —NH-(TtbRW)—Z, —NH-(TtbWR)—Z, —NH-(TtbRR)—Z, —NH-(TtbWW)—Z, —NH—(RTtbTtb)-Z, —NH—(WTtbTtb)-Z, —NH-(TtbTtbR)-Z, —NH-(TtbTtbW)—Z, —NH-(TtbRTtb)-Z, —NH-(TtbWTtb)-Z, and —NH-(TtbTtbTtb)-Z; and Z is H, or Ac; provided that at least one of $R^4$ and $R^5$; and at least one of $R^5$, $R^6$, and $R^7$, contains a Ttb residue.

In one embodiment, with respect to the peptide according to formula Ia, the peptide is according to formula VIIa, VIIb, VIIc, VIId, VIIe, or VIIf:

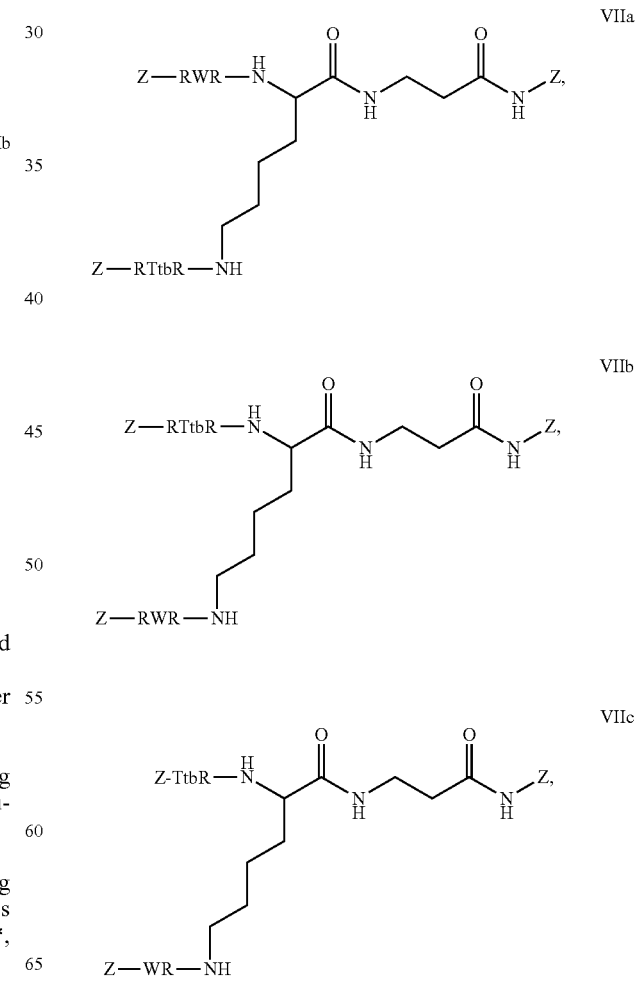

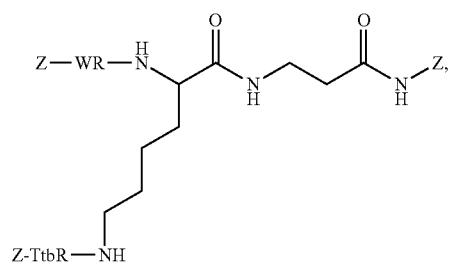
VIId
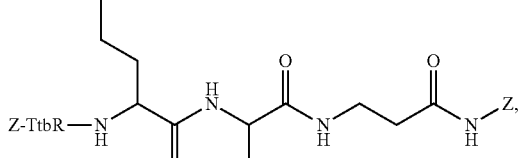
VIIIb
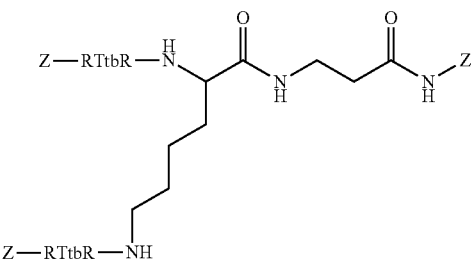
VIIe
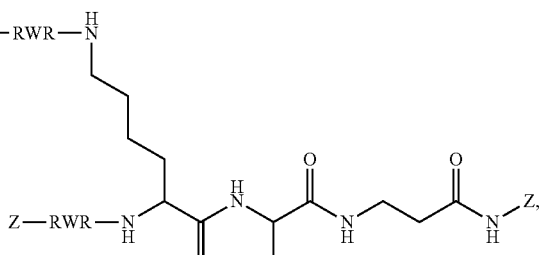
VIIIc
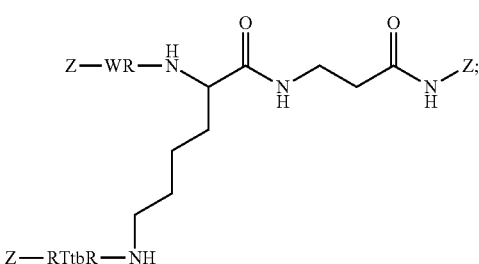
VIIf
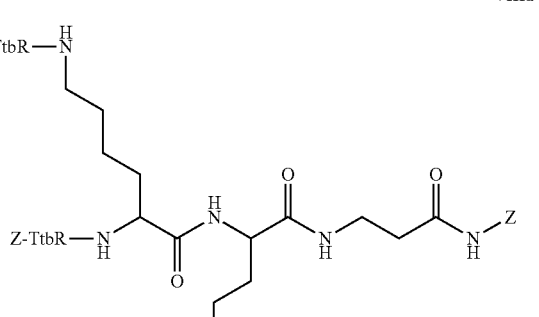
VIIId
wherein each Z is independently H, or Ac.
In one embodiment, with respect to the peptide according to formula Ia, the peptide is according to formula VIIIa, VIIIb, VIIIc, VIIId, VIIIe, or VIIIf:
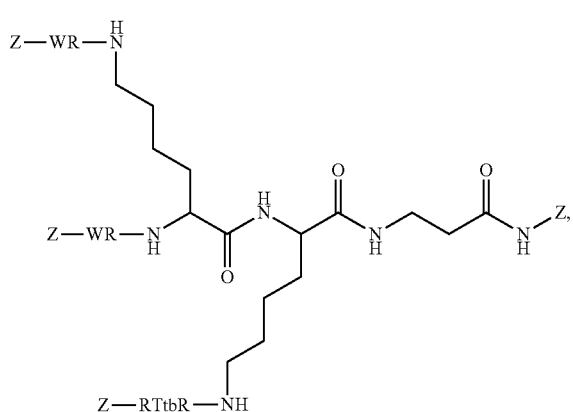
VIIIa
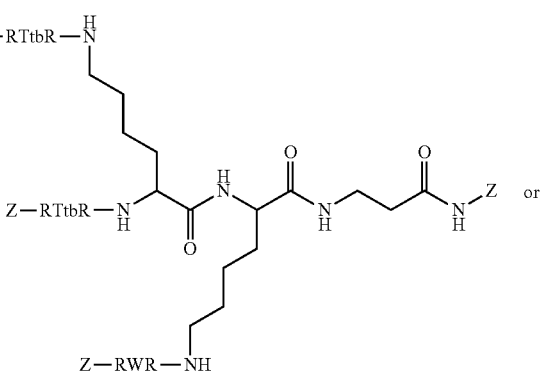
VIIIe -continued VIIIf

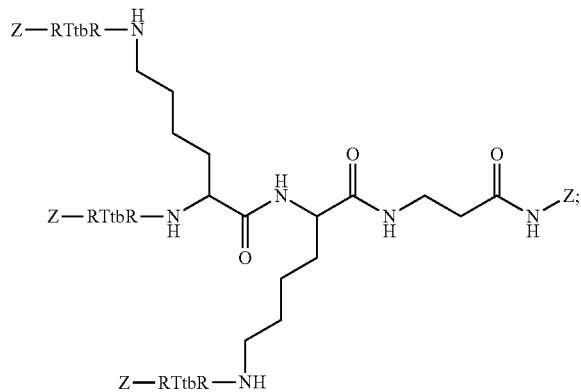

wherein each Z is independently H, or Ac.

In one embodiment, with respect to the peptide according to formula Ia, and VIa-VIIIf, Z is H.

In one embodiment, with respect to the peptide according to formula Ia, and VIa-VIIIf, Z is Ac.

In certain aspects and where appropriate, the present invention extends to the preparation of prodrugs and derivatives of the peptides of the invention. Prodrugs are derivatives which have cleavable groups and become by solvolysis or under physiological conditions the peptide of the invention, which are pharmaceutically active, in vivo.

In certain aspects and where appropriate, the present invention provides a method for preventing, treating, ameliorating or managing a disease or condition which comprises administering to a patient in need of such prevention, treatment, amelioration or management, a prophylactically or therapeutically effective amount of the pharmaceutical composition of the peptides described herein.

In one embodiment, with respect to the method, the disease or condition is or results from a bacterial infection.

In one embodiment, with respect to the method, the disease or condition is or results from a viral infection.

In one embodiment, with respect to the method, the disease or condition is or results from a fungal infection.

In one embodiment, the disease or condition is or results from a bacterial infection.

In one embodiment, the disease or condition is or results from gram positive or gram negative bacterial strains. The compositions of the present invention can be used to kill or inhibit the growth of any of the following microbes or mixtures of the following microbes, or, alternatively, can be administered to treat local and/or systemic microbial infections or illnesses caused by the following microbes or mixtures of the following microbes: Gram-positive cocci, for example Staphylococci (*Staph. aureus, Staph. epidermidis*) and Streptococci (*Strept. agalactiae, Strept. faecalis, Strept. pneumoniae, Strept. pyogenes*); Gram-negative cocci (*Neisseria gonoirhoeae* and *Yersinia pestis*) and Gram-negative rods such as Enterobacteriaceae, for example *Escherichia coli, Hamophilus influenzae, Citrobacter* (*Citrob. freundii, Citrob. divernis*), *Salmonella* and *Shigella*, and *Francisella* (*Francisella tularensis*); Gram-positive rods such as *Bacillus* (*Bacillus anthracis, Bacillus thuringenesis*); furthermore *Klebsiella* (*Klebs. pneumoniae, Klebs. oxytoca*), *Enterobacter* (*Ent. aerogenes, Ent. agglomerans*), *Hafnia, Serratia* (*Serr. marcescens*), *Proteus* (*Pr. mirabilis, Pr. rettgeri, Pr. vulgaris*), *Providencia, Yersinia*, the genus *Acinetobacter*, and the genus *Brevibacterium*, including *Brevibacterium* linens, which is ubiquitously present on human skin and is the causative agent of foot odor. Furthermore, the antimicrobial spectrum of the peptides of the present invention may cover the genus *Pseudomonas* (*Ps. aeruginosa, Ps. maltophilia*), the aerotolerant anaerobic gram positive bacterium *Propionibacterium acnes* (*P. acnes*), which is causatively linked to skin acne, and strictly anaerobic bacteria such as, for example, *Bacteroides fragilis*, representatives of the genus *Peptococcus, Peptostreptococcus* and the genus *Clostridium*; furthermore *Mycoplasmas* (*M. pneumoniae, M. hominis, Ureaplasma urealyticum*) as well as *Mycobacteria*, for example *Mycobacterium tuberculosis*. This list of microbes is purely illustrative and is in no way to be interpreted as restrictive.

In one embodiment, the disease or condition is or results from Methicillin-resistant *Staphylococcus aureus* (MRSA).

Examples of microbial infections or illness that can be treated by administration of a peptide or peptides of the present invention or a composition thereof include, but are not limited to, microbial infections or illnesses in, for example, humans such as, for example, otitis, pharyngitis, pneumonia, peritonitis, pyelonephritis, cystitis, endocarditis, systemic infections, bronchitis (acute and chronic), sepsis, illnesses of the upper airways, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmon, wound infections, infected burns, burns, infections in the mouth (including, e.g., but not limited to, periodontal disease and gingivitis), infections after dental operations, osteomyelitis, septic arthritis, cholecystitis, peritonitis with appendicitis, cholangitis, intraabdominal abscesses, pancreatitis, sinusitis, mastoiditis, mastitis, tonsileitis, typhoid, meningitis and infections of the nervous system, salpingitis, endometritis, genital infections, pelveoperitonitis and eye infections.

In one embodiment, the disease or condition is or results from a viral infection. Examples of viral infections that can be treated by administration of a peptide or peptides of the present invention or a composition thereof include, but are not limited to, viral infections caused by human immunodeficiency virus (HIV-1, HIV-2), hepatitis virus (e.g., hepatitis A, hepatitis B, hepatitis C, hepatitis D, and hepatitis E viruses), herpesviruses (e.g. herpes simplex virus types 1 and 2, varicella-zoster virus, cytomegalovirus, Epstein Barr virus, and human herpes viruses types 6, 7, and 8), influenza virus, respiratory syncytial virus (RSV), vaccinia virus, and adenoviruses. This list is purely illustrative and is in no way to be interpreted as restrictive.

It will be appreciated by skilled practitioners that subjects suffering from viral illnesses frequently succumb to secondary bacterial and/or fungal infections. Accordingly, in an embodiment of the invention pertaining to treating a disease or condition associated with a viral infection, an attending physician will be monitoring the patient for signs indicating the onset of such a secondary infection.

In one embodiment, the disease or condition is or results from a fungal infection. Examples of fungal infections or illnesses that can be treated by administration of a peptide or peptides of the present invention or a composition thereof include, but are not limited to, fungal infections caused by Chytridiomycetes, Hyphochrytridiomycetes, Plasmodiophoromycetes, Oomycetes, Zygomycetes, Ascomycetes, and Basidiomycetes. Fungal infections which can be inhibited or treated with compositions of the peptides provided herein include, but are not limited to: Candidiasis, including, but not limited to, onchomycosis, chronic mucocutaneous candidiasis, oral candidiasis, epiglottistis, esophagitis, gastrointestinal infections, genitourinary infections, for example, caused by any *Candida* species, including, but not limited to, *Candida albicans, Candida tropicalis, Candida (Torulopsis) glabrata, Candida parapsilosis, Candida lusitaneae, Candida rugosa* and *Candida pseudotropicalis*; Aspergillosis, including, but not limited to, granulocytopenia caused, for example, by, *Aspergillus* spp. Including, but not limited, to *Aspergillus fumigatus, Aspergillus favus, Aspergillus niger* and *Aspergillus terreus; Zygomycosis*, including, but not limited to, pulmonary, sinus and rhinocerebral infections caused by, for example, zygomycetes such as *Mucor, Rhizopus* spp., *Absidia, Rhizomucor, Cunningamella, Saksenaea, Basidobolus* and *Conidobolus; Cryptococcosis*, including, but not limited, to infections of the central nervous system, e.g., meningitis, and infections of the respiratory tract caused by, for example, *Cryptococcus neoformans*; Trichosporonosis caused by, for example, *Trichosporon beigelii*; Pseudallescheriasis caused by, for example, *Pseudallescheria boydii; Fusarium* infection caused by, for example, *Fusarium* such as *Fusarium solani, Fusarium moniliforme* and *Fusarium proliferartum*; and other infections such as those caused by, for example, *Penicillium* spp. (generalized subcutaneous abscesses), *Trichophyton* spp., for example, *Trichophyton mentagrophytes* and *Trichophyton rubrum, Stachybotrys* spp., for example, *S. chartarum, Drechslera, Bipolaris, Exserohilum* spp., *Paecilomyces lilacinum, Exophila jeanselmei* (cutaneous nodules), *Malassezia furfur* (folliculitis), *Alternaria* (cutaneous nodular lesions), *Aureobasidium pullulans* (splenic and disseminated infection), *Rhodotorula* spp. (disseminated infection), *Chaetomium* spp. (empyema), *Torulopsis candida* (fungemia), *Curvularia* spp. (nasopharnygeal infection), *Cunninghamella* spp. (pneumonia), *H. Capsulatum, B. dermatitidis, Coccidioides immitis, Sporothrix schenckii* and *Paracoccidioides brasiliensis, Geotrichum candidum* (disseminated infection). The peptides and compositions of the present invention can also be used to kill or inhibit the growth of any of the fungi listed above. This list is purely illustrative and is in no way to be interpreted as restrictive.

In a further aspect, the present invention provides a method for preventing, treating, ameliorating or managing a disease or condition, which comprises administering to a patient in need of such prevention, treatment, amelioration or management a prophylactically or therapeutically acceptable amount of a peptide described herein, or the pharmaceutical composition of peptides described herein, wherein the disease or condition results from or is caused by bacterial infection, viral infection or fungal infection.

In a further aspect, the present invention provides a therapeutic composition comprising a peptide composition of the invention, prepared as a hydrogel.

Pharmaceutical Compositions

When employed as pharmaceuticals, the peptide compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptide compounds in combination with one or more non-peptide antibiotic compounds, including known antibiotic compounds. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptide compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate may be added as a lubricant. The mixture may then be formed into 240-270 mg tablets (80-90 mg of active compound per tablet) in a tablet press.

Formulation 2

Capsules

A compound of the invention may be admixed as a dry powder with a starch diluent in an approximate 1:1 weight ratio. The mixture may then be filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

The present complexes may be used as therapeutic agents for the treatment of conditions in mammals. Accordingly, the complexes and pharmaceutical compositions of this invention find use as therapeutics for preventing and/or treating infections and like maladies resulting from bacterial, viral or fungal attack, and related conditions in mammals, including humans.

In a method of treatment aspect, this invention provides a method of treating a mammal afflicted with a condition associated with or resulting from bacterial, viral or fungal attack or infection, which method comprises administering an effective amount of one or more of the pharmaceutical compositions just described.

In additional method of treatment aspects, this invention provides methods of treating a mammal afflicted with a variety of bacteria or other infections, including strains which have developed resistance to traditional antibiotics, such as, for example, *Staphylococcus aureus*. The method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as viral or microbial conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

The complexes of this invention can be administered as the sole active agent or they can be administered in combination with other agents, including other active derivatives.

The methods disclosed herein have veterinary applications and can be used to treat a wide variety of non-human vertebrates. Thus, in other aspects of the invention, the peptides and compositions of the present invention are administered in the above methods to non-human vertebrates, such as wild, domestic, or farm animals, including, but not limited to, cattle, sheep, goats, pigs, dogs, cats, and poultry such as chicken, turkeys, quail, pigeons, ornamental birds and the like.

The following are examples of microbial infections in non-human vertebrates that can be treated by administering the peptides or compositions of the present invention: Pig: coli diarrhoea, enterotoxaemia, sepsis, dysentery, salmonellosis, metritis-mastitis-agalactiae syndrome, mastitis; ruminants (cattle, sheep, goat): diarrhoea, sepsis, bronchopneumonia, salmonellosis, pasteurellosis, mycoplasmosis, genital infections; horse: bronchopneumonias, joint ill, puerperal and post-puerperal infections, salmonellosis; dog and cat: bronchopneumonia, diarrhoea, dermatitis, otitis, urinary tract infections, prostatitis; poultry (chicken, turkey, quail, pigeon, ornamental birds and others): mycoplasmosis, *E. coli* infections, chronic respiratory tract illnesses, salmonellosis, pasteurellosis, psittacosis. This list is purely illustrative and is in no way to be interpreted as restrictive.

In additional method of treatment aspects, this invention provides methods of treating a mammal afflicted with a variety of bacteria or other infections, including strains which have developed resistance to traditional antibiotics, such as, for example, *Staphylococcus aureus*. Accordingly, the method comprises administering an effective condition-treating amount of one or more of the pharmaceutical compositions just described.

The peptide antimicrobials of the invention may also be used in preventive or prophylactic applications, wherein the peptide antimicrobials are administered to a subject for preventive purposes (i.e., administered to a subject in advance of exposure to a disease causing entity) individually or as a combination of different peptide antimicrobials. The peptide antimicrobials of the invention can also be used in combination with antibiotics administered in a preventive application. A number of antibiotics are used clinically to reduce the risk of contracting bacterial, viral, and/or fungal infections. Ideally such preventive or prophylactic administration prevents infection.

In general, prophylactic administration of antibiotics is recommended only in certain situations or for people with particular medical problems. People with abnormal heart valves, for example, have a high risk of developing heart valve infections even after minor surgery. Such infections occur because bacteria from other parts of the body can enter the bloodstream during surgical procedures and travel to the heart valves. To prevent these infections, people with abnormal heart valves often take antibiotics before having any kind of surgery, including dental surgery.

Antibiotics may also be prescribed to prevent infections in people with weakened immune systems such as those with Acquired Immune Deficiency Syndrome (AIDS) or people who are having chemotherapy treatments for cancer. Even healthy people with strong immune systems, however, may occasionally be given preventive antibiotics if they are scheduled to have surgery that is associated with a high risk of infection, or if they are traveling to parts of the world where they are likely to contract an infection that causes, for example, diarrhea.

Drugs used for antibiotic prophylaxis include: amoxicillin (a type of penicillin) and fluoroquinolones such as ciprofloxacin (Cipro) and trovafloxacin (Trovan). These drugs are available in tablet, capsule, liquid, and injectable forms. Other antibiotics used for prophylactic purposes are known to those skilled in the art.

The following list presents particular embodiments wherein antibiotics are used for preventive purposes, wherein the peptide antimicrobials of the invention may also be used to advantage either alone or in combination with prophylactic antibiotics. For malaria prophylaxis, clinicians prescribe 100 mg (e.g., doxycycline) by mouth daily 1-2 weeks prior to travel then 4 weeks after travel. For AIDS patients, *pneumocystis carinii* pneumonia prophylaxis is recommended and generally involves administration of Bactrim (trimethoprim-sulfamethoxazole), double strength tablet, one tablet by mouth daily. For AIDS patients, suppression of cryptococcal meningitis relapse is recommended and generally involves administration of fluconazole, 200 mg daily. Patients with other immunocompromising conditions (e.g., bone marrow transplant patients and neutropenic patients on chemotherapy) are also prescribed prophylactic oral antibiotics to prevent opportunistic infections by common fungal or bacterial agents.

For surgical prophylaxis, the cephalosporin antibiotics are usually preferred. This class includes cefazolin (Ancef, Kefzol), cefamandole (Mandol), cefotaxime (Claforan), and others. The choice of drug depends on its spectrum and the type of bacteria that are most likely to be encountered. Surgery on the intestines, for example, which are filled with many anaerobic bacteria, might call for cefoxitin (Mefoxin), while in heart surgery, where there are no anaerobes, cefazolin might be preferred.

The following list presents particular embodiments wherein antibiotics are used for surgical prophylaxis, wherein the peptide antimicrobials of the invention may also be used to advantage either alone or in combination with prophylactic antibiotics. For patients with valvular heart disease, patients with a history of any valvular heart disease may be administered oral amoxicillin prior to dental work. Patients with a history of major valvular heart disease (like a valve replacement) may be administered iv antibiotics (usually ampicillin, 1 gram every 6 hours and gentamicin 80 mg every 8 hours) prior to, during and after major abdominal surgery.

As pre-operative antibiotics, any patient having abdominal surgery may be treated with antibiotics intravenously (iv). Typically, patients receive one dose of a cephalosporin (Cefotetan, Cefoxitin, etc.), about 1 gram iv. For heavy intra-operative bleeding or operations lasting longer than 4 hours, another dose of iv antibiotics may be given and, in extended use, iv antibiotics may be administration for 24 hours after the operation. For bowel surgery, general surgeons will frequently administer iv Ciprofloxacin 400 mg and Metronidazole 500 mg. In cases of emergency surgery, post-operative antibiotics are usually given to prevent infection. In all cases, the antibiotic administered is determined by the attending medical practitioner, based on experience as to which microbial agents the patient is most likely to be exposed.

A skilled practitioner would appreciate applications wherein the peptide antimicrobials of the invention may be used to advantage, alone or in conjunction with antibiotics for prophylactic purposes. In a particular embodiment, peptide antimicrobials of the invention may be administered alone or in conjunction with antibiotics for preventing bacterial infections.

Antimicrobial Substrates

The peptides of the present invention and compositions thereof may also be bound to or incorporated into substrates to provide antimicrobial substrates to reduce or inhibit microbial contamination of the substrate. The present invention also provides articles comprising the antimicrobial substrates of the invention.

As indicated above, a skilled practitioner would take into consideration such variables as the likelihood of microbial contamination of a substrate prior to or during use, risks associated with microbial contamination in a subject using a substrate, and duration of use.

Substrates suitable for the present invention include conventional polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising the aforementioned polymers, which may further comprise or may be functionalized to comprise active groups with which peptides of the invention may react, and which allow for immobilization of same. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer. Various methods of protein or peptide immobilization are described in Protein Immobilization (Richard F. Taylor (ed.), Marcel Dekker, New York, 1991).

Substrates suitable for the present invention also include ceramics, glass, metal, metal oxides, and composites comprised of ceramics, glass, metal or metal oxides plus polymers as described above. Suitable metals include steel, stainless steel, aluminum, copper, titanium, alloys thereof, and combinations thereof.

The articles of the present invention have antimicrobial peptides of the invention bound to or incorporated into a substrate. The use of antimicrobial peptides to confer antimicrobial properties to substrates provides many advantages due to the fact that the peptides of the invention exhibit biocidal activity, broad spectrum activity, and a reduced likelihood of resistance in target organisms compared to more traditional antimicrobials, such as antibiotics. Peptides can be bound to a substrate either physicochemically, or covalently. Physicochemical binding of peptides to a substrate may occur by any one or combinations of the following forces: electrostatic, hydrogen bonding, and Van der Waals. Alternatively, peptides may be bound to the substrate surface by a covalent bond. Additionally, antimicrobial peptides of the present invention can be incorporated into the polymer by mixing with the polymer, for example by dissolving the peptides and the polymer in a common solvent and casting or molding the peptide:polymer mixture into an article.

In one embodiment, antimicrobial peptides are bound to the substrate by coating a substrate polymer with an aqueous or non-aqueous solution of the peptide, wherein the peptide is at a concentration ranging from about 0.0001 to about 20 weight percent. The peptides are contacted with the substrate polymer, and the peptides and substrate polymer are optionally shaken at temperatures ranging from about −10° C. to about 150° C. for a period of time ranging from about 0.1 min to about 96 hrs. Preferably the peptides and substrate polymer are shaken at a temperature of from about 25° C. to about 80° C. for a period of time ranging from about 1 min to about 24 hrs.

In another embodiment, the substrate polymer is primed to generate active groups that will bind to the antimicrobial peptides. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous or non-aqueous solution of from about 0.001 to about 20 weight percent of the antimicrobial peptide. The peptide and the polymer may be shaken at temperatures ranging from about −10° C. to about 150° C. for a period of time ranging from about 0.1 min to about 96 hrs. Preferably the peptide and substrate polymer are shaken at a temperature of from about 25° C. to about 80° C. for a period of time ranging from about 10 min to about 24 hrs.

In another embodiment, a commercial substrate polymer containing 1-50% active groups is brought into contact with an aqueous or non-aqueous solution comprising from about 0.0001 to about 20 weight percent of the antimicrobial peptide.

Methods for binding or incorporating peptides to substrates are known to those of skill in the art who would, moreover, be aware of additional modifications to the above general guidelines that could be implemented, as required, to improve binding or incorporation of the peptides of the invention to substrates. U.S. Pat. No. 7,307,061, for example, describes such methods in detail and is incorporated herein in its entirety.

After treatment with the antimicrobial peptide, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise an extrudate, film, membrane, laminate, knit fabric, woven fabric, non-woven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include those for lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial peptide of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, or child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as peripheral IV catheters and central venus catheters comprised of either polyurethane or silicon, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy. Additional child-oriented articles that benefit from the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

As used herein and referred to in the art, a biofilm is an aggregate of microbes with a distinct architecture. A biofilm is essentially a collective in which microbial cells, each only a micrometer or two long, form towers that can be hundreds of micrometers high. The channels between the towers act as fluid-filled conduits that circulate nutrients, oxygen, waste products, etc., as required to maintain a viable biofilm community. The biofilm or microbial (bacterial, fungal, or algal) community is typically enveloped by extracellular biopolymers produced by the microbial cells and adheres to the interface between a liquid and surface. The encapsulated property of biofilms renders the microbial organisms therein highly resistant to standard anti-microbial therapeutics. Bacteria growing in a biofilm, for example, are highly resistant to antibiotics, and in some cases are up to 1,000 times more resistant than the same bacteria growing without a biofilm superstructure. Standard antibiotic therapy can be useless wherein a biofilm contaminated implant is detected and the only recourse under such circumstances may be to remove the contaminated implant. Fungal biofilms also frequently contaminate medical devices. They can cause chronic vaginal infections and lead to life-threatening systemic infections in immunocompromised individuals. Biofilms are, furthermore, involved in numerous diseases. Cystic fibrosis patients, for example, suffer from *Pseudomonas* infections that often result in antibiotic resistant biofilms.

The antimicrobial peptides of the invention are well suited to applications directed to the prevention of biofilm formation or eradication of a pre-existing biofilms because they act quickly and exhibit broad spectrum activity. As indicated herein above, these advantageous properties also apply to other uses of the antimicrobial peptides of the invention.

In order to impart antimicrobial functionality to the products listed, the product can be treated with an antimicrobial peptide of the invention before it is manufactured, or after, or at any time during manufacture of the product. For example, in making an antimicrobial shower curtain, antimicrobial peptides of the invention may be bound to or incorporated into the polymer substrate, followed by fashioning a shower curtain from the treated material. Alternatively, treatment of the polymer substrate with antimicrobial peptides of the invention may be performed after the substrate is made into a shower curtain.

Antimicrobial substrates or articles prepared by methods of the invention exhibit antimicrobial functionality, wherein microbes are killed, or microbial growth is reduced or prevented. Antimicrobial activity of the antimicrobial substrate or article can be determined by using any of a number of methods well known in the art, such as the Shake Flask Test described in U.S. Pat. No. 7,307,061 and United States Patent Application No. 2008/0081789, the entire contents of which are incorporated herein in their entireties. Additional methods for determining antimicrobial activity are discussed in Tenover et al. (eds.), Manual of Clinical Microbiology, 7.sup.th Edition, Section VIII, 1999, American Society for Microbiology, Washington, D.C.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptides that have been listed hereinabove. The peptides of the invention may be prepared from known or commercially available starting materials and reagents by one skilled in the art of organic synthesis.

Abbreviations

DIC=diisopropylcarbodiimide;
DCM=dichloromethane
4-AMP=4-(aminomethyl)piperidine
HBTU=2-(1H-benzotriazol-1-yl-1,1,3,3-tetramethyluronium hexafluorophosphate
HOBT=1-hydroxybenzotriazole
DIEA=diisopropylethylamine
DEA=diethylamine
DCHA=dicyclohexylamine
DMF=dimethylformamide
TFA=trifluoroacetic acid
TIS=triisopropylsilane
Boc=tert-butyloxycarbonyl
Fmoc=9-fluorenemethyloxycarbonyl
Pmc=2,2,5,7,8-pentamethylchroman-6-sulfonyl Representative Synthetic Method Preparation of Dendrimeric Peptides of the Invention The following representative amino acids are used for "A" (m=1):
Trp (W)
Phe (F)
Lys (K)
Arg (R) and
Try (Y).
The following representative "A" dipeptides (m=2) are used to prepare peptides of the invention.
RW
RW*
RF
RY
R-2Nal
H*W
KW
KY and
KF.
The following representative "A" dipeptides (m=3) can be used to prepare peptides of the invention.
RWW
RFF
RYY
KWW
KYY and
KFF.

The dendrimeric antimicrobial peptides in accordance with a first embodiment of the invention can be prepared using the representative synthetic pathway depicted in Scheme 1.

Scheme 1

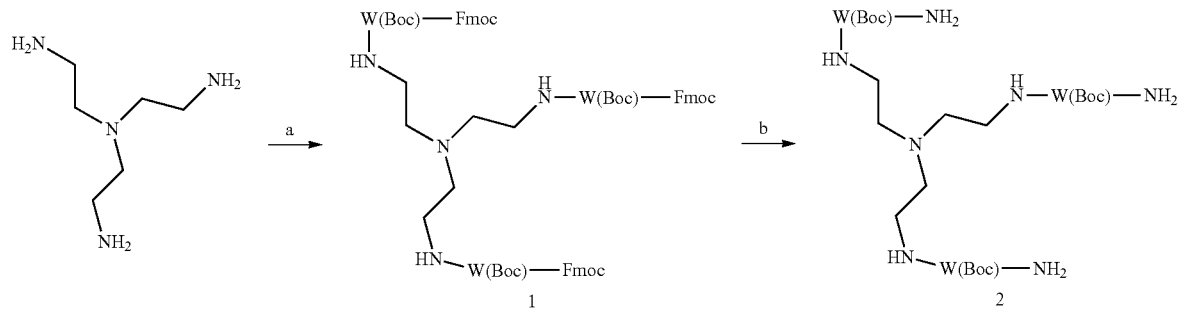

-continued

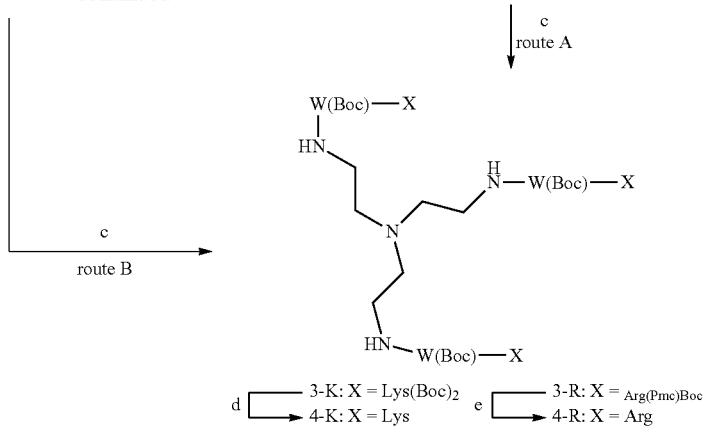

Scheme 1. Conditions and Reagents: a) Fmoc—Trp(Boc)—OH, DIC, DCM, 18 h, yield 85%, b) 4-AMP, DCM, 1 h, yield 78%; c) (route A): Boc—Lys(Boc)—OH·DCHA or Boc—Arg(Pmc)—OH, HBTU, HOBT, DIEA, DMF, 4 h, yield 76.5% (3-K), 64% (3-R); (route B): (i) DEA, DCM, 1.5 h, then, (ii) Boc—Arg(Pmc)—OH, HBTU, HOBT, DIEA, DMF, 4 h, yield 85% (3-R), d) TFA/Water/TIS (90:5:5), 1 h, yield 70.5%; e) Reagent B [TFA/Phenol/Water/TIS (88:5:5:2)], 1.5-2 h, yield 80.3%.

TAEA-(W(Boc)-Fmoc)$_3$ (1).

To a stirred solution of Fmoc-Trp(Boc)-OH (3.3 mmol, 1.74 g) and diisopropylcarbodiimide (3.3 mmol, 511 µL) in methylene chloride (20 mL), was added tris(2-aminoethyl) amine (1 mmol, 149.5 µL) and the mixture was stirred overnight at room temperature. TLC (CHCl$_3$/MeOH=90:10) indicated that the reaction was complete. The reaction mixture was diluted to a volume of 40 mL with CH$_2$Cl$_2$. The solution was then washed with saturated NaCl (1×20 mL), saturated KHSO$_4$ (1×20 mL) and saturated NaCl (1×20 mL). After drying over Na$_2$SO$_4$, the solvent was evaporated in vacuum and the residue was chromatographed on silica gel to give a colorless oil, which was recrystallized from CH$_2$Cl$_2$/hexane to give the pure product (1.42 g, 85%).

ESI-MS: m/z=Found 1672.8 (M+H$^+$) Calcd 1672.2

TAEA-(W(Boc)-NH$_2$)$_3$ (2).

To a stirred solution of 1 (0.733 mmol, 1.23 g) in CH$_2$Cl$_2$ (15 mL), was added 4-aminomethylpiperidine (1.5 mL), and the mixture was stirred for 1 h. The course of the reaction was controlled by TLC (CHCl$_3$/MeOH=90:10). The suspension was filtered, the precipitate was washed with portions of CH$_2$Cl$_2$ and the filtrate was diluted to a volume of 45 mL with EtOAc. The solution was then washed with saturated NaCl (1×20 mL), phosphate buffer pH 5.5 (3×20 mL) and saturated NaCl (1×20 mL). After drying over Na$_2$SO$_4$, the solvent was evaporated in vacuum to give the unprotected product 2 (573.9 mg, 78%).

ESI-MS: m/z=Found 1005.6 (M+H$^+$); 1027.6 (M+Na$^+$), Calcd 1005.2; 1027.2

TAEA-(W(Boc)R(Pmc)-Boc)$_3$ (3-R).

Route A:

Without further purification, 2 (0.475 mmol, 477 mg) was dissolved in DMF (15 mL) and Boc-Arg(Pmc)-OH (1.57 mmol, 848.9 mg), HBTU (1.57 mmol, 595.5 mg), HOBT (1.57 mmol, 212.2 mg), DIEA (3.14 mmol, 547.2 µL), were added to the reaction mixture which was stirred for 4 h at room temperature. The solvent was evaporated and EtOAc (40 mL) was added. The solution was then washed with saturated KHSO$_4$ (1×20 mL), saturated NaHCO$_3$ (1×20 mL), and saturated NaCl (1×20 mL). After drying over Na$_2$SO$_4$, the solvent was evaporated to afford the crude product which was chromatographed on silica gel and was recrystallized from CH$_2$Cl$_2$/hexane to give 3-R (787 mg, 64%).

Route B:

To a stirred solution of 1 (0.74 mmol, 1.24 g) in CH$_2$Cl$_2$ (10 mL), was added diethylamine (5 mL), and the mixture was stirred for 1.5 h to ensure complete removal of Fmoc protecting group. The course of the reaction was monitored by TLC. Solvent was evaporated and the residue was washed with two portions of CH$_2$Cl$_2$ to remove residual DEA. Without further purification, the resulting oil was dissolved in DMF (15 mL) and Boc-Arg(Pmc)-OH (2.44 mmol, 1.32 g), HBTU (2.44 mmol, 925.5 mg), HOBT (2.44 mmol, 329.7 mg), DIEA (1.874 mmol, 850.4 µL), were added to the reaction mixture which was stirred for 4 h at room temperature. The solvent was evaporated and EtOAc (40 mL) was added. The solution was then washed with saturated KHSO$_4$ (1×20 mL), saturated NaHCO$_3$ (1×20 mL), and saturated NaCl (1×20 mL). After drying over Na$_2$SO$_4$, the solvent was evaporated in vacuum to give the crude product which was chromatographed on silica gel and was recrystallized from CH$_2$Cl$_2$/hexane to give 3-R (1.62 g, 85%).

ESI-MS: m/z=Found 1287.3 (MH$_2^{2+}$); Calcd 1287.1

TAEA-(W(Boc)K(Boc)-Boc)$_3$ (3-K).

Without further purification, 2 (0.696 mmol, 699 mg) was dissolved in DMF (25 mL) and Boc-Lys(Boc)-OH·DCHA (2.3 mmol, 1.21 g), HBTU (2.3 mmol, 872.4 mg), HOBT (2.3 mmol, 310.8 mg), DIEA (4.6 mmol, 801.6 µL), were added to the reaction mixture which was stirred for 4 h at room temperature. The solvent was evaporated and EtOAc (40 mL) was added. The solution was then washed with saturated KHSO$_4$ (1×20 mL), saturated NaHCO$_3$ (1×20 mL), and saturated NaCl (1×20 mL). After drying over Na$_2$SO$_4$, the solvent was evaporated in vacuum to give a yellow oil which was purified by flash chromatography to give 3-K (1.06 g, 76.5%).

ESI-MS: m/z=Found 1991.2 (M+H$^+$); Calcd 1991.4

TAEA-(WR—NH$_2$)$_3$ (4-R) (Compound 1).

To 200 mg (0.078 mmol) of the Boc-protected 3-R, was added 5 mL of Reagent B [TFA/Phenol/Water/Tis] (88:5:5:2, v/v) and the resulting mixture was stirred for 1.5-2 h at room temperature, then TFA was evaporated and the residue was precipitated with ether. The precipitate was washed with cold ether (three times) and dried under dry N₂ gas to give the TFA-salt of 4-R as white solid (116 mg, 80.3%) with purity >90%.

The crude product was purified by preparative RP-HPLC to remove minor impurities, using C-18 column, and eluting with H₂O+0.1% TFA (eluent A) and CH₃CN+0.1% TFA (eluent B). Elution gradient: 0-100% CH₃CN in 40 min and flow rate=7 mL/min. The resulting pure product was collected and lyophilized to reduce TFA and any residual solvents.

ESI-MS: m/z=Found 587.2 (MH$_2^{2+}$); 1173.8 (M); Calcd 587.7; 1173.4

TAEA-(WK—NH₂)₃ (4-K) (Compound 2).

To 543 mg (0.273 mmol) of the Boc-protected 3-K, was added 5 mL of TFA/Water/TIS (90:5:5, v/v) and the resulting mixture was stirred for 1 h at room temperature, then the volume was reduced and the product was precipitated with cold ether. The precipitate was filtered, washed with cold ether three times and dried under vacuo to give the heptatrifluoroacetate salt of 4-K (363 mg, 70.5%) with purity >90%.

The crude product was purified by preparative RP-HPLC to remove minor impurities, using C-18 column, and eluting with H₂O+0.1% TFA (eluent A) and CH₃CN+0.1% TFA (eluent B). Elution gradient: 0-100% CH₃CN in 40 min and flow rate=7 mL/min. The resulting pure product was collected and lyophilized to reduce TFA and any residual solvents.

ESI-MS: m/z=Found 1111.8 (M+Na⁺); Calcd 1112.5.

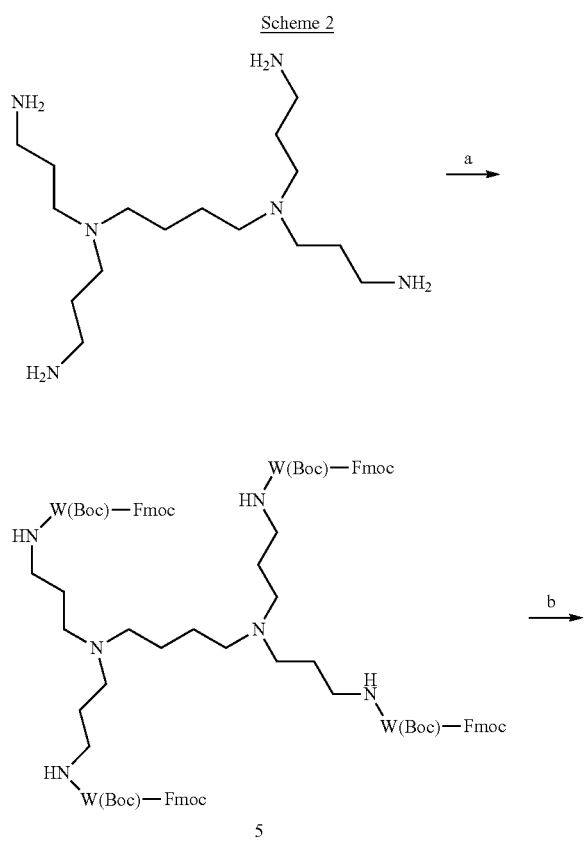

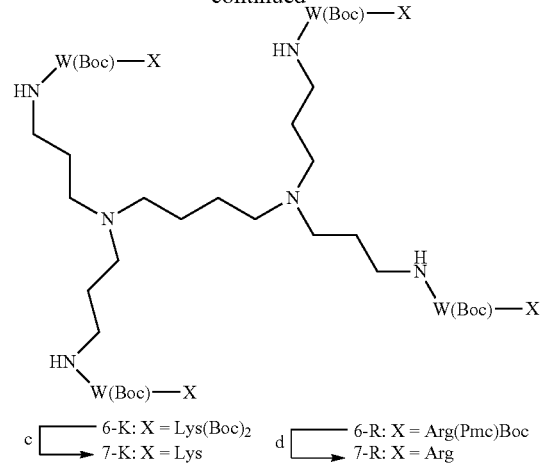

Scheme 2. Conditions and Reagents: a) Fmoc—Trp(Boc)—OH, DIC, DCM, 18 h, yield 93%; b) (i) DEA, DCM 1 h, (ii) Boc—Lys(Boc)—OH·DCHA or Boc—Arg(Pmc)—OH, HBTU, HOBT, DIEA, DMF, 4 h, yield 70% (3-K), 69% (3-R); c) TFA/Water/TIS (90:5:5), 1 h, yield 96%; e) Reagent B [TFA/Phenol/Water/TIS (88:5:5:2)], 1.5-2 h, yield 97%.

POPAM-(W(Boc)-Fmoc)₃ (5).

To a stirred solution of Fmoc-Trp(Boc)-Ol-1 (2.2 mmol, 1.16 g) and diisopropylcarbodiimide (2.2 mmol, 340.7 µL) in methylene chloride (20 mL), was added N,N,N',N'-Tetrakis (3-aminopropyl)-1,4-butanediamine (0.5 mmol, 164.9 µL) and the mixture was stirred overnight (20 h) at room temperature. The reaction mixture was diluted to a volume of 40 mL with CH₂Cl₂. The solution was then washed with saturated NaCl (1×20 mL), saturated KHSO₄ (1×20 mL) and saturated NaCl (1×20 mL). After drying over Na₂SO₄, the solvent was evaporated in vacuum to give a colourless oil which was chromatographed on silica gel and was recrystallized from CH₂Cl₂/hexane to give the pure product (1.1 g, 93%).

ESI-MS: m/z=Found 1176.2 (MH$_2^{2+}$); Calcd 1176.4

POPAM-(W(Boc)K(Boc)-Boc)₃ (6-K).

To a stirred solution of 5 (0.213 mmol, 500 mg) in CH₂Cl₂ (10 mL), was added Diethylamine (5 mL), and the mixture was stirred for 1.5 h to ensure complete removal of Fmoc protecting group. The course of the reaction was monitored by TLC. Solvent was evaporated and the residue was washed with two portions of CH₂Cl₂ to remove residual DEA. Without further purification, the resulting oil was dissolved in DMF (15 mL) and Boc-Lys(Boc)-OH.DCHA (0.937 mmol, 494.6 mg), HBTU (0.937 mmol, 355.5 mg), HOBT (0.937 mmol, 126.7 mg), DIEA (1.874 mmol, 326.6 µL), were added to the reaction mixture which was stirred for 4 h at room temperature. The solvent was evaporated and EtOAc (20 mL) was added. The solution was then washed with saturated KHSO₄ (1×10 mL), saturated NaHCO₃ (1×10 mL), and saturated NaCl (1×10 mL). After drying over Na₂SO₄, the solvent was evaporated in vacuum to give the crude product which was purified by flash chromatography [EtOAc/MeOH/TEA (90:8:2); R$_f$=0.33] to afford 6-K as a colorless oil (415 mg, 70%).

ESI-MS: m/z=Found 1388.6 (MH$_2^{2+}$); Calcd 1388.7

POPAM-(W(Boc)R(Pmc)-Boc)₃ (6-R).

To a stirred solution of 5 (0.213 mmol, 500 mg) in CH₂Cl₂ (10 mL), was added Diethylamine (5 mL), and the mixture was stirred for 1.5 h to ensure complete removal of Fmoc protecting group. The course of the reaction was monitored by TLC. Solvent was evaporated and the residue was washed with two portions of CH₂Cl₂ to remove residual DEA. Without further purification, the resulting oil was dissolved in DMF (15 mL) and Boc-Arg(Pmc)-OH (0.937 mmol, 506.8 mg), HBTU (0.937 mmol, 355.5 mg), HOBT (0.937 mmol, 126.7 mg), DIEA (1.874 mmol, 326.6 µL), were added to the reaction mixture which was stirred for 4 h at room temperature. The solvent was evaporated and EtOAc (20 mL) was added. The solution was then washed with saturated $KHSO_4$ (1×10 mL), saturated $NaHCO_3$ (1×10 mL), and saturated NaCl (1×10 mL). After drying over $Na_2SO_4$, the solvent was evaporated in vacuum to give the crude product which was purified by flash chromatography [from 100% EtOAc ($R_f$=0) to EtOAc/MeOH/TEA (80:18:2); $R_f$=0.52] to afford 6-R as a colorless foam (525 mg, 69%).

ESI-MS: m/z=Found 1777.0 ($MH_2^{2+}$); 1185.0 ($MH_3^{3+}$); Calcd 1777.2; 1185.1

POPAM-(WR—$NH_2$)$_3$ (7-R) (Compound 3).

To 356 mg (0.1 mmol) of the Boc-protected 6-R, was added 5 mL of Reagent B [TFA/Phenol/Water/Tis] (88:5:5:2, v/v) and the resulting mixture was stirred for 1.5-2 h at room temperature, then TFA was evaporated and the residue was precipitated with ether. The precipitate was washed with cold ether (three times) and dried under dry $N_2$ gas to give the TFA-salt of 7-R as white solid (275 mg, 97%) with purity >90%.

The crude product was purified by preparative RP-HPLC to remove minor impurities, using C-18 column, and eluting with $H_2O$+0.1% TFA (eluent A) and $CH_3CN$+0.1% TFA (eluent B). Elution gradient: 0-100% $CH_3CN$ in 40 min and flow rate=7 mL/min. The resulting pure product was collected and lyophilized to reduce TFA and any residual solvents.

ESI-MS: m/z=Found 844.0 ($MH_2^{2+}$); 1686.2 ($M^+$); Calcd 844.6; 1687.2

POPAM-(WK—$NH_2$)$_3$ (7-K) (Compound 4).

To 278 mg (0.1 mmol) of the Boc-protected 6-K, was added 5 mL of TFA/Water/TIS (90:5:5, v/v) and the resulting mixture was stirred for 1 h at room temperature, then the volume was reduced and the product was precipitated with cold ether. The precipitate was filtered, washed with cold ether three times and dried under vacuo to give the trifluoroacetate salt of 7-K (260 mg, 96%) with purity >90%.

The crude product was purified by preparative RP-HPLC to remove minor impurities, using C-18 column, and eluting with $H_2O$+0.1% TFA (eluent A) and $CH_3CN$+0.1% TFA (eluent B). Elution gradient: 0-100% $CH_3CN$ in 40 min and flow rate=7 mL/min. The resulting pure product was collected and lyophilized to reduce TFA and any residual solvents. ESI-MS: m/z=Found 787.9 ($MH_2^{2+}$); 1574.1 ($M^+$); 1597.0 ($M+Na^4$); Calcd 788.3; 1574.7; 1597.7

Representative Synthetic Method

Preparation of Tta (Trialkyltryptophan) Containing Dendrimeric Peptides of the Invention The Tta incorporated dendrimeric antimicrobial peptides in accordance with the invention can be prepared using the representative synthetic pathway depicted in Scheme 3. The representative Tta incorporported dendrimeric peptides prepard according to the following methods are presented in Table 2.

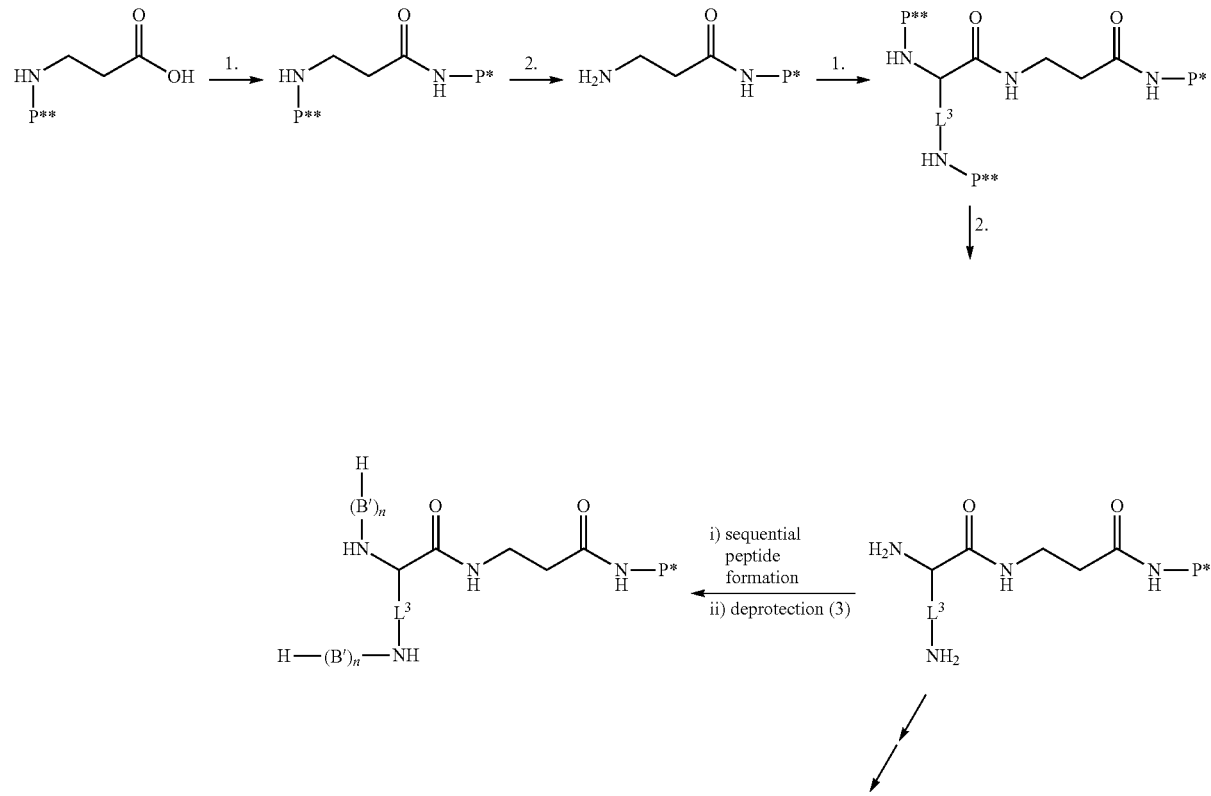

Scheme 3

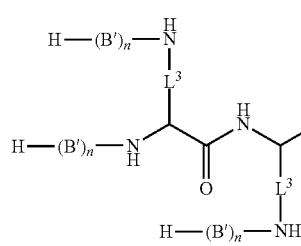
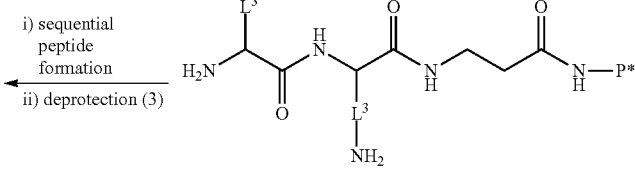

-continued i) sequential peptide formation
ii) deprotection (3)

wherein p*-Rink amide resin, P**-Fmoc
1. HOBt/HBTU/DIEA
2. Piperidine
3. 95% TFA/2.5% TIS/2.5% H₂O;
and L³, B' and n are described herein.

First, an Fmoc-protected β-alanine residue, making up the C-terminus, is coupled to Rink amide resin. This residue is deprotected and coupled to Fmoc-Lys(Fmoc)-OH with Fmoc-protected α- and ε-amino groups. Using the same protecting group for both amino groups allows for simultaneous deprotection, so that two amide bonds are formed during the next coupling step. Divalent, trivalent, and tetravalent cores can be achieved by following or repeating this step. In effect, up to 4 free amino groups are created respectively.

Crude peptides are deprotected by 95% TFA, 2.5% water, 2.5% TIS, precipitated in ether and purified on reverse phase HPLC. Molecular weights are verified by M/S using a Bruker MALDI-TOF spectrometer, which are in agreement with theoretical masses.

The following representative amino acids are used to prepare the peptides of the invention:

Trp (W)
Phe (F)
Lys (K)
Arg (R)
Try (Y) and
Ttb.

The following additional representative amino acids are used to prepare the peptides of the invention.

RW
RW*
RF
RY
R-2Nal
H*W
KW
KY
KF and
RTtb.

The following additional representative amino acids are used to prepare the peptides of the invention.

RWW
RFF
RYY
KWW
KYY
KFF and
RTtbR.

Synthesis of Tta (Trialkyltryptophan) Intermediates

Synthesis of Boc-Ttb-OH and Fmoc-Ttb-OH

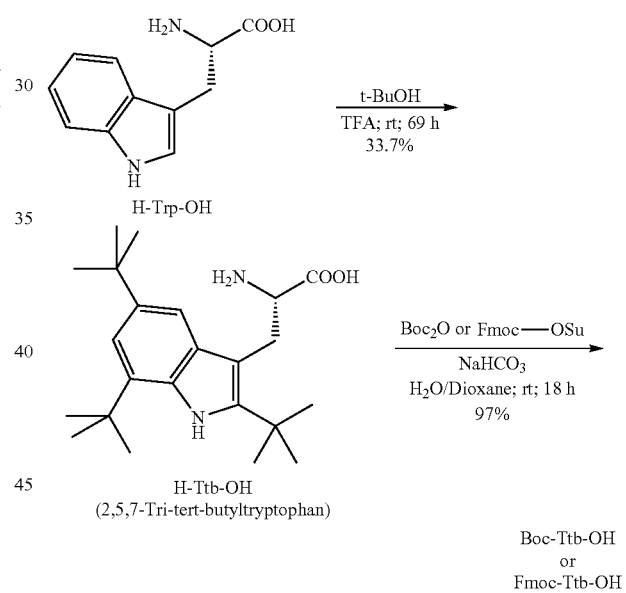

Scheme 4

2,5,7-Tri-tert-Butyltryptophan(H-Ttb-OH)

A mixture of H-Trp-OH (10.0 g, 49 mmol) and t-butanol (38.67 g, 0.52 mol) in trifluoroacetic acid (150 mL) was stirred at room temperature for 69 h. The resulting dark solution was evaporated to give a dark oily material. Water was added and the resulting suspension was neutralized with aq. KHCO₃. Constant trituration of the mixture during addition of the base resulted in the formation of a pinkish gum like material. The aqueous layer was decanted off, and the gum like material was re-crystallized twice from 50% ethanol in water to yield the title compound as colorless solid (33.7% Yield).

Boc-Ttb-OH or Fmoc-Ttb-OH

To a solution of H-Ttb-OH (2.0 g, 5.37 mmol) in water/dioxane 1:1 (80 mL), was added Boc₂O [or Fmoc-OSu] (5.37 mmol), and NaHCO$_3$ (1.35 g, 16.11 mmol). The resulting mixture was stirred at room temperature for 18 h. The solvents were evaporated and the residual solid was mixed with ethyl acetate and 5% KHCO$_3$ in water. The aqueous phase was extracted twice more with ethyl acetate, and the combined organic phases were washed with 5% KHCO$_3$ and saturated aq. NaCl and dried over anhyd. Na$_2$SO$_4$. The solvent was evaporated under vacuum to yield the title compound as a yellow foam (97% Yield). The crude product was used without further purification.

Synthesis of the Tta containing Peptides

Synthesis of 2D-04 and 2D-24 (Table 2)

the resin and the mixture was stirred overnight. After DMF and DCM washes, the unreacted amines were capped with a Ac$_2$O/DIEA/DMF (1:2:2) mixture to give a final loading of 0.25 mmol/g. Upon Fmoc-deprotection, a mixture of Fmoc-Lys(Fmoc)-OH (4 eq), HBTU (4 eq), HOBT (4 eq) and DIEA (8 eq) in DMF was added and the resin was stirred for 1 h. After removal of Fmoc-group, Fmoc-Arg (Pbf)-OH (8 eq) was added using HBTU/HOBT/DIEA as activating reagent. Subsequent Fmoc-deprotection and addition of Fmoc-Trp (Boc)-OH (16 eq) or Fmoc-Ttb-OH were carried out. Upon final coupling with Fmoc-Arg (Pbf)-OH (8 eq) and final Fmoc-deprotection, the dendrimers 2D-04 and 2D-24 were cleaved from the resin using TFA/Water/Triispropylsilane (95:2.5:2.5) mixture and precipitated with ether. The crude

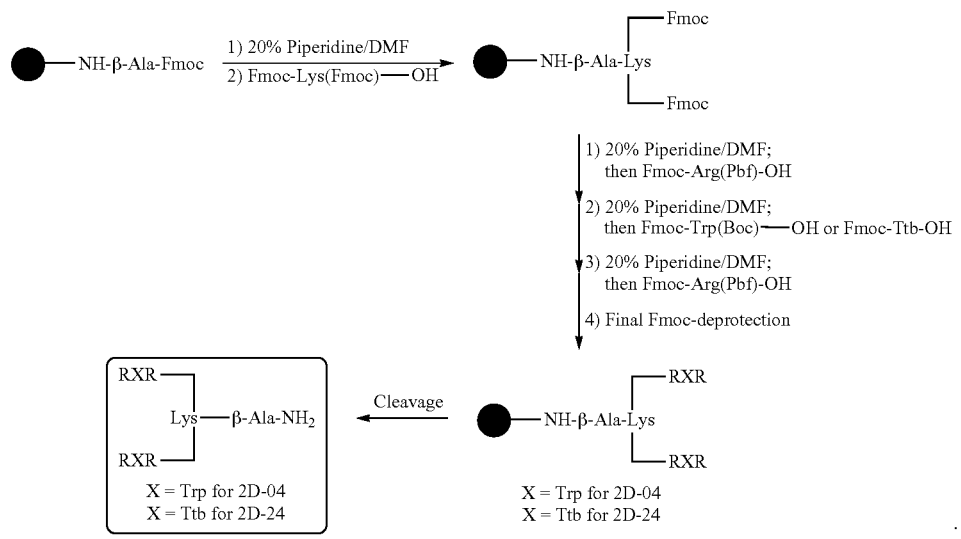

The synthesis of the dibranched lysine core dendrimers 2D-04 and 2D-24 was performed manually by stepwise solid phase procedure on rink amide resin. The resin (100 mg, 0.62 mmol/g) was swelled in dichloromethane for 1 h, and 20% piperidine/DMF (2×10 min) was added to remove the Fmoc-protecting group. Fmoc-β-Ala-OH (25 μmol) was added to dendrimers were purified by RP-HPLC and characterized by MALDI-TOF, which gave masses consistent with the final products.

Synthesis of 3D-03, 3D-13, 3D-23, 3D-06, 3D-16 and 3D-26 (Table 2)

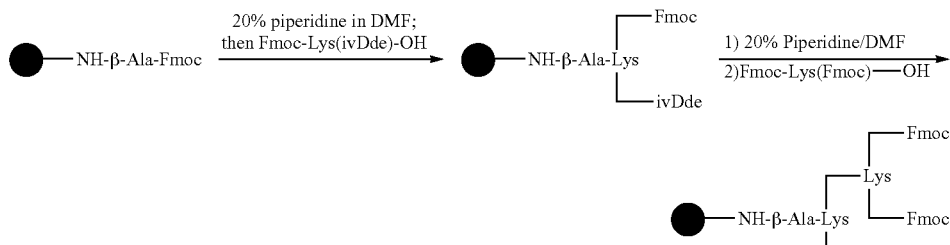

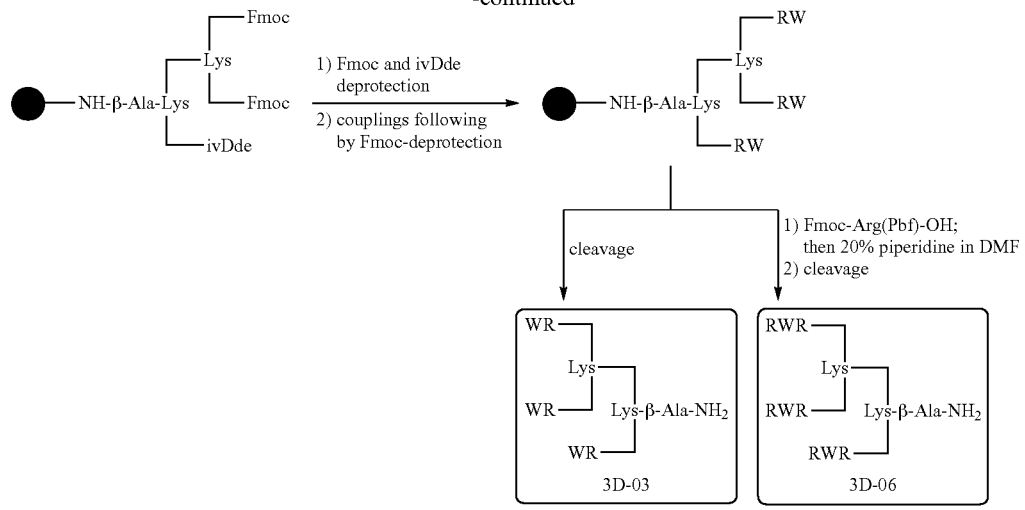
B)
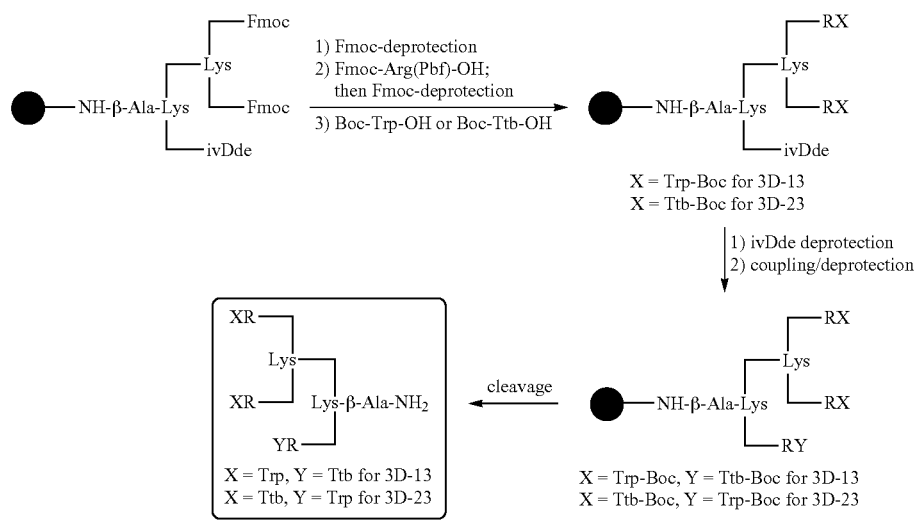
C)
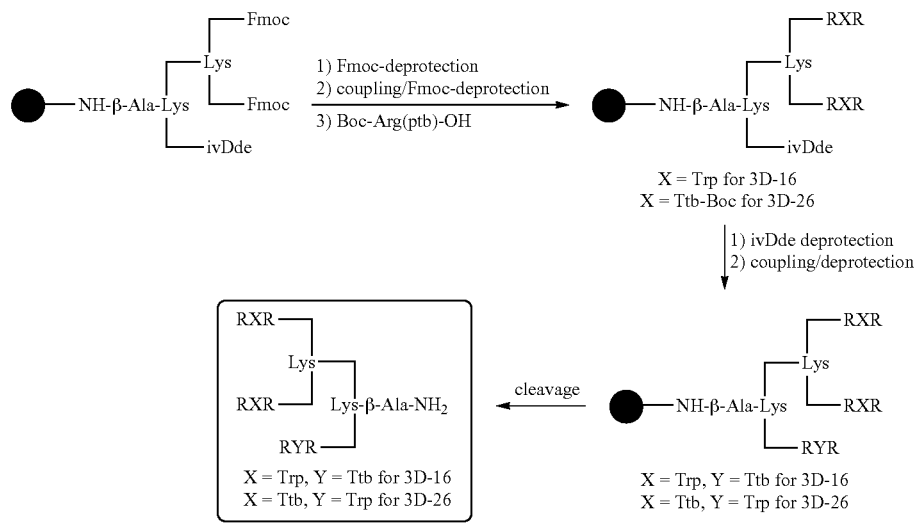

The synthesis of 3D-03, 3D-13, 3D-23, 3D-06, 3D-16 and 3D-26 was performed as follows:
(i) The first level of core was achieved using 4 eq of Fmoc-Lys(ivDde)-OH. Half part of the subsequent level was built by adding 4 eq of Fmoc-Lys(Fmoc)-OH.
(ii) 3D-03 and 3D-06: starting from (i) and following Fmoc and ivDde removals, three RW-dipeptide or RWR-tripeptide residues were attached using subsequently Fmoc-Arg (Pbf)-OH (12 eq), Fmoc-Trp(Boc)-OH (12 eq). Final Fmoc-deprotection and cleavage with TFA/Tis/Water (95: 2.2:2.5) give the crude products.
(iii) 3D-13, 3D-23, 3D-16 and 3D-26: starting from (i) and following Fmoc removal, two Boc-protected RX-dipeptide or RXR-tripeptide (X=Tip or Ttb) residues were attached. The remaining third branch of the core was built by treatment with 2% hydrazine/DMF and subsequent coupling with a third RX-dipeptide or RXR-tripeptide. Upon completion of the synthesis, the dendrimers were cleaved from the resin using a TFA/Tis/Water (95:2.2:2.5) mixture for 3D-16 and 3D-26 or a TFA/Phenol/Water/Thioanisole/EDT/TIS (81.5:5:5:5:2.5:1) mixture for 3D-13 and 3D-23. The other Tta (trialkyltryptophan) containing peptides can be synthesized using the general procedures described above and substituting the Ttb with the appropriate Tta derivative.

All crude products were purified by RP-HPLC using (water+0.1% TFA) and (acetonitrile+0.1% TFA) as eluents. The pure products were characterized by MALDI-TOF, which gave masses consistent with the final products.

EXAMPLES

The following examples are presented in order to more fully illustrate the preferred embodiments of the invention. They should in no way be construed, however, as limiting the broad scope of the invention.

Example 1

Antibacterial Activity

The antibacterial activity of each dendrimer peptide was tested by following standard broth microdilution protocols recommended by the National Committee for Clinical Laboratory Standard (NCCLS 2004). Antibacterial testing was carried out on gram-negative bacteria $E.\ coli$ (D31) and gram-positive bacteria $S.\ aureus$ in liquid media Mueller Hinton (MH) Broth according to literature procedures. Dendrimers were dissolved in PBS buffer (high salt, 150 mM NaCl; low salt, 75 mM NaCl), pH 7.4 to make series of stocks of 2-fold dilution. Cultures were grown overnight on Mueller Hinton (MH) agar plates, and 3 to 5 uniform colonies of each organism were transferred with an inoculating loop to test tubes containing MH broth, and incubated at 37° C. overnight, then diluted until the turbidity matched that of the 0.5 McFarland standard (approximately $1.5 \times 10^8$ cells/mL). The resulting solutions were further diluted to give approximately $2 \times 10^4$-$2 \times 10^5$ CFU/mL. 100 µL of the bacterial inoculums were incubated in 96-well plates with varying volumes of stock solution and PBS buffer to bring the total volume to 200 µL. Solutions containing the same volumes of PBS buffer and MH Broth, with and without bacteria were used as controls. After these plates were incubated with shaking for 18 hrs at 37° C. to ensure the cultures had reached log phase growth, the absorbance readings were recorded at a wavelength of 600 nm using a Absorbance Microplate Reader BIO-TEK ELX800. The 18-hour absorbance data were used to calculate the percent inhibition for each test condition. All assays were carried out in triplicate. The experimental data were fitted to sigmoidal dose-response curves using GraphPad Prism (GraphPad Software Inc., San Diego, Calif., USA). The concentration of dendrimer that resulted in 50% inhibition of growth was recorded as $IC_{50}$ (Table 1 and 3).

Hemolytic Assays

Hemolytic activity of dendrimeric compounds were assessed on fresh sheep RBC (Fitzgerald, Inc., MA). Dendrimer concentrations corresponding to 50% hemolysis were used as hemolytic dose (HD50) determined from dose-response curve. The fresh sheep RBC was washed with PBS buffer (thrice) and aliquots of cell suspension were mixed in eppendorf tubes with varying volumes of stocks and buffer for a total volume of 400 µL. These tubes were incubated at 37° C. for 1 hr, and then spun down at 3,000 rpm for 5 mins. The resulting supernatant was trasferred to a 96-well plate and the absorbances at 540 nm were measured in an Absorbance Microplate Reader BIO-TEK ELX800. Zero hemolysis and 100% hemolysis controls were obtained by incubating the cells with buffer and 1% Triton X-100, respectively. Hemolytic index (HI) was defined as $HI = HD_{50}/IC_{50}$ (Table 1 and 3).

TABLE 1

Antimicrobial activity and Hemolysis data for the Dedrimers according to Formula I

| Dendrimer | E. Coli $IC_{50}$ (ug/mL) | HI | S. Aureus $IC_{50}$ (ug/mL) | HI | Hemolysis $HD_{50}$ (ug/mL) |
|---|---|---|---|---|---|
| POPAM-(WR)$_4$ (7-R) | 0.57 ± 0.12 | 511 | 0.37 ± 0.13 | 786 | 291 |
| POPAM-(WK)$_4$ (7-K) | 0.76 ± 0.01 | 1883 | 0.51 ± 0.06 | 1431 | 730 |
| TAEA-(WR)$_3$ (4-R) | 2.07 ± 0.22 | 1485 | 0.97 ± 0.02 | 3168 | 3073 |
| TAEA-(WK)$_3$ (4-K) | 6.87 ± 0.01 | 789 | 4.12 ± 0.58 | 1316 | 5423 |
| (RW)$_{4D}$ | 4.5 | 310 | 16 | 88 | 1400 |

TABLE 2
Representative Tta Containing Peptide Dendrimers
| ID (nD-xy)[a] | Chemical structure | Mass (M + H+) Expected (Found) |
|---|---|---|
| 3D-03* | 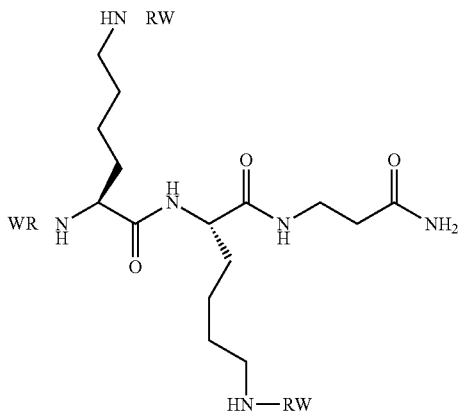 | 1371.70 (1371.88) |
| 3D-13 | 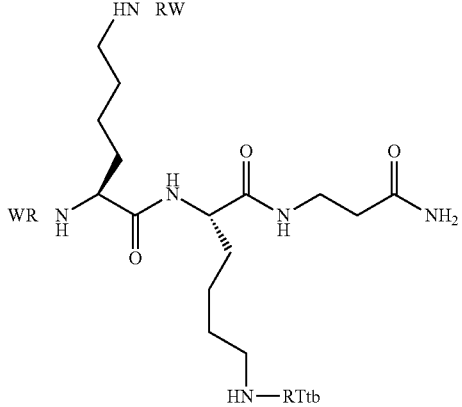 | 1539.80 (1539.98) |
| 3D-23 | 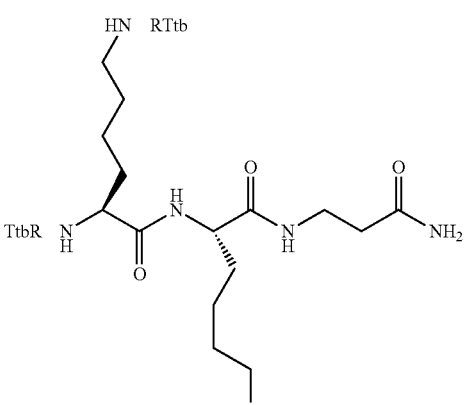 | 1707.90 (1708.14) |

TABLE 2-continued

Representative Tta Containing Peptide Dendrimers

| ID (nD-xy)[a] | Chemical structure | Mass (M + H+) Expected (Found) |
|---|---|---|
| 3D-06* | (structure) | 1840.20 (1840.09) |
| 3D-16 | (structure) | 2008.20 (2007.94) |
| 3D-26 | (structure) | 2176.20 (2176.13) |
| 2D-04* | (structure) | 1214.20 (1213.54) |

TABLE 2-continued

Representative Ttb Containing Peptide Dendrimers

| ID (nD-xy)[a] | Chemical structure | Mass (M + H+) Expected (Found) |
|---|---|---|
| 2D-24 | (structure) | 1550.20 (1549.88) |
| 4D-04* | (structure) | 1843.20 (1843.44) |

[a] n = number of branches; x = number of Ttb (2,5,7-tri-tert-butyltryptophan) residues; y = number of arginine residues;
*reference peptides

TABLE 3

Antimicrobial activity and Hemolysis data for Ttb containing Dendrimers

| AMP code | Overall charge | Bulky Trp/Ttb | IC$_{50}$ (μg/mL) E. Coli D31 | MRSA | B. Subtilis | HD$_{50}$ (μg/mL) Hemolysis |
|---|---|---|---|---|---|---|
| 3D-03 | +6 | 3/0 | 12.1 | >100 | 14.3 | 3197 |
| 3D-13 | +6 | 2/1 | 1.0 | 1.7 | 1.9 | 270 |
| 3D-23 | +6 | 1/2 | 2.4 | 0.7 | 2.1 | 99 |
| 3D-06 | +9 | 3/0 | 1.8 | 17.3 | 1.9 | 2336 |
| 3D-16 | +9 | 2/1 | 0.4 | 5.2 | 0.9 | 201 |
| 3D-26 | +9 | 1/2 | 1.4 | 0.5 | 1.4 | 33 |
| 2D-04 | +6 | 2/0 | 6.8 | 56.6 | 6.1 | 3428 |
| 2D-24 | +6 | 0/2 | 0.5 | 0.2 | 0.8 | 48 |
| 4D-04 (ref) | +8 | 4/0 | 4.5 | 14.6 | 4.2 | 1563 |

From the above data, it can be seen that these dendrimeric AMPs show potent broad-spectrum antibacterial activity.

REFERENCES

Bogusz, S., Boxer, A., and Busath, D. D. 1992. An Ss1-Ss2 Beta-Barrel Structure for the Voltage-Activated Potassium Channel. *Protein Engineering* 5: 285-293.

Braun, P., and von Heijne, G. 1999. The aromatic residues Trp and Phe have different effects on the positioning of a transmembrane helix in the microsomal membrane. *BIOCHEMISTRY-US* 38: 9778-9782.

Case, D. A., Darden, T. A., Cheatham, T. E., Simmerling, I., C. L., Wang, J., Duke, R. E., Luo, R., Merz, K. M., Wang, B., Pearlman, D. A., et al. 2004. AMBER 8, University of California, San Francisco.

Chattopadhyay, A., and McNamee, M. G. 1991. Average Membrane Penetration Depth of Tryptophan Residues of the Nicotinic Acetylcholine-Receptor by the Parallax Method. *BIOCHEMISTRY-US* 30: 7159-7164.

de Planque, M. R. R., and Killian, J. A. 2003. Protein-lipid interactions studied with designed transmembrane peptides: role of hydrophobic matching and interfacial anchoring (Review). *Molecular Membrane Biology* 20: 271-284.

Deisenhofer, J., and Michel, H. 1989. The Photosynthetic Reaction Center from the Purple Bacterium *Rhodopseudomonas*-Viridis. *Science* 245: 1463-1473.

Durell, S. R., and Guy, H. R. 1992. Atomic Scale Structure and Functional Models of Voltage-Gated Potassium Channels. *Biophysical Journal* 62: 238-250.

Han, M., Chen, P. Q., and Yang, X. Z. 2005. Molecular dynamics simulation of PAMAM dendrimer in aqueous solution. *Polymer* 46: 3481-3488.

Hancock, R. E., and Diamond, G. 2000. The role of cationic antimicrobial peptides in innate host defences. *Trends in microbiology* 8: 402-410.

Hancock, R. E., and Chapple, D. S. 1999. Peptide antibiotics. *Antimicrob Agents Chemother* 43: 1317-1323.

Henderson, R., Baldwin, J. M., Ceska, T. A., Zemlin, F., Beckmann, E., and Downing, K. H. 1990. Model for the Structure of Bacteriorhodopsin Based on High-Resolution Electron Cryomicroscopy. *Journal of Molecular Biology* 213: 899-929.

Hu, W., Lee, K. C., and Cross, T. A. 1993. Tryptophans In Membrane-Proteins—Indole Ring Orientations And Functional Implications In The Gramicidin Channel. *BIOCHEMISTRY-US* 32: 7035-7047.

Ketchem, R. R., Hu, W., and Cross, T. A. 1993. High-Resolution Conformation Of Gramicidin-A In A Lipid Bilayer By Solid-State Nmr. *Science* 261: 1457-1460.

Killian, J. A., and von Heijne, G. 2000. How proteins adapt to a membrane-water interface. *Trends in Biochemical Sciences* 25: 429-434.

Koeppe, R. E., Killian, J. A., and Greathouse, D. V. 1994. Orientations of the Tryptophan 9 and 11 Side-Chains of the Gramicidin Channel Based on Deuterium Nuclear-Magnetic-Resonance Spectroscopy. *Biophysical Journal* 66: 14-24.

Landoltmarticorena, C., Williams, K. A., Deber, C. M., and Reithmeier, R. A. F. 1993. Nonrandom Distribution of Amino-Acids in the Transmembrane Segments of Human Type-I Single Span Membrane-Proteins. *Journal of Molecular Biology* 229: 602-608.

Lehrer, R. I., and Ganz, T. 1999. Antimicrobial peptides in mammalian and insect host defence. *Curr Opin Immunol* 11: 23-27.

Meers, P. 1990. Location of Tryptophans in Membrane-Bound Annexins. *BIOCHEMISTRY-US* 29: 3325-3330.

Mishra, V. K., Palgunachari, M. N., Segrest, J. P., and Anantharamaiah, G. M. 1994. Interactions of Synthetic Peptide Analogs of the Class a Amphipathic Helix with Lipids—Evidence for the Snorkel Hypothesis. *Journal of Biological Chemistry* 269: 7185-7191.

Reithmeier, R. A. F. 1995. Characterization And Modeling Of Membrane-Proteins Using Sequence-Analysis. *Current Opinion In Structural Biology* 5: 491-500.

Ridder, A., Morein, S., Stam, J. G., Kuhn, A., de Kruijff, B., and Killian, J. A. 2000. Analysis of the role of interfacial tryptophan residues in controlling the topology of membrane proteins. *BIOCHEMISTRY-US* 39: 6521-6528.

Schiffer, M., Chang, C. H., and Stevens, F. J. 1992. The Functions Of Tryptophan Residues In Membrane-Proteins. *Protein Engineering* 5: 213-214.

Sieprawska-Lupa, M., Mydel, P., Krawczyk, K., Wojcik, K., Puklo, M., Lupa, B., Suder, P., Silberring, J., Silberring, J., Reed, M., et al. 2004. Degradation of human antimicrobial peptide LL-37 by *Staphylococcus aureus*-derived proteinases. *Antimicrobial Agents and Chemotherapy* 48: 4673-4679.

Strandberg, E., and Killian, J. A. 2003. Snorkeling of lysine side chains in transmembrane helices: how easy can it get? *Febs Letters* 544: 69-73.

Torchilin, V., and Weissig, V. 2003. Liposomes: A Practical Approach; second edition.Oxford University Press, London, UK.

van 't H of, W., Veerman, E. C. I., Helmerhorst, E. J., and Amerongen, A. V. N. 2001. Antimicrobial peptides: Properties and applicability. *Biological Chemistry* 382: 597-619.

Vonheijne, G. 1992. Membrane-Protein Structure Prediction—Hydrophobicity Analysis and the Positive-inside Rule. *Journal of Molecular Biology* 225: 487-494.

Vonheijne, G. 1994. Membrane-Proteins—from Sequence to Structure. *Annual Review of Biophysics and Biomolecular Structure* 23: 167-192.

Wimley, W. C., and White, S. H. 1996. Experimentally determined hydrophobicity scale for proteins at membrane interfaces. *Nature Structural Biology* 3: 842-848.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for nucleic acids or polypeptides are approximate, and are provided for description.

All publications, including but not limited to patents and patent applications, cited in this specification are herein incorporated by reference as if each individual publication were specifically and individually indicated to be incorporated by reference herein as though fully set forth.

What is claimed is:

1. A pharmaceutical composition for treating or managing a disease or condition caused by bacteria; wherein the pharmaceutical composition comprises a peptide according to formula I:

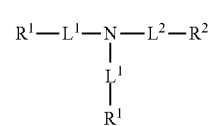

wherein
$L^1$ is independently unsubstituted $C_{2-5}$ alkylene;
$L^2$ is unsubstituted $C_{3-5}$ alkylene;
each $R^1$ is independently
—NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, —NH—FK—Z, —NH—RWW—Z, —NH—RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z,
or

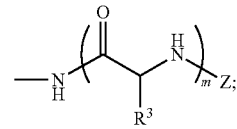

m is 1, 2, 3, or 4; each Z is independently H, Ac, or any other conventional N-protecting group;
$R^3$ is unsubstituted alkyl, aralkyl, heteroarylalkyl, aminoalkyl, or guanidinoalkyl;
$R^2$ is $R^1$; or $R^2$ is —N($L^1$-$R^1$)$_2$;
and
Tta is 2,5,7-trialkyltryptophan residue;
or a pharmaceutically acceptable salt thereof.

2. The pharmaceutical composition according to claim 1, wherein the peptide is according to formula II, IIIa, or IIIb:

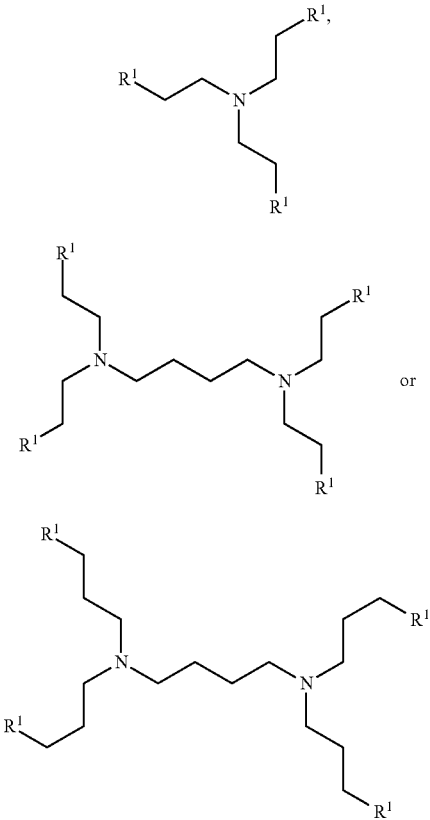

and each $R^1$ is as in claim 1.

3. The pharmaceutical composition according to claim 1, wherein each $R^1$ is independently —NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, —NH—FK—Z, —NH—RWW—Z, —NH—RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z; and Z is H or Ac.

4. The parmaceutical composition according to claim 1 wherein $R^2$ is —N($L^1$-$R^1$)$_2$.

5. The pharmaceutical composition according to claim 1, wherein the peptide is according to formula IIIa or IIIb:

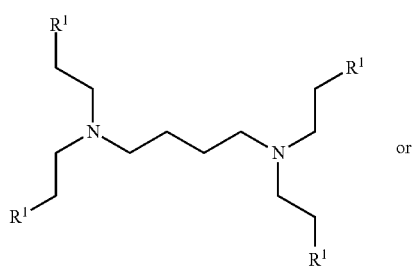

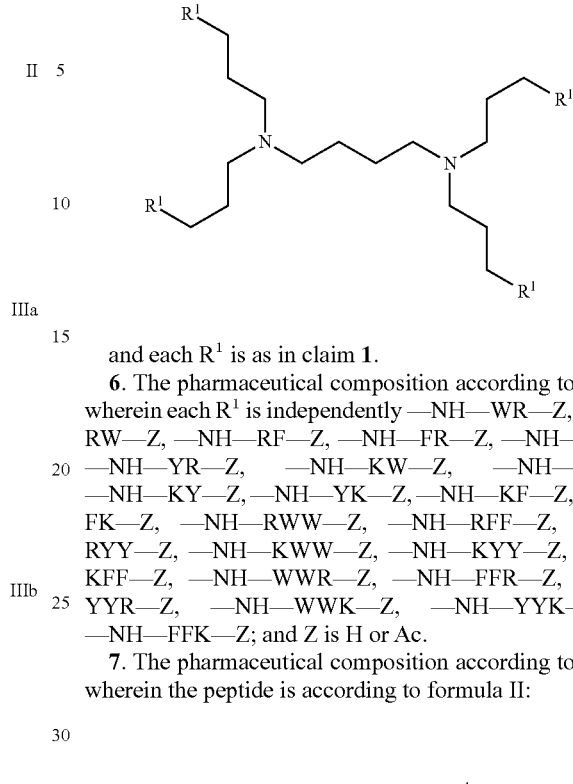

and each $R^1$ is as in claim 1.

6. The pharmaceutical composition according to claim 4, wherein each $R^1$ is independently —NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, —NH—FK—Z, —NH—RWW—Z, —NH—RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z; and Z is H or Ac.

7. The pharmaceutical composition according to claim 1, wherein the peptide is according to formula II:

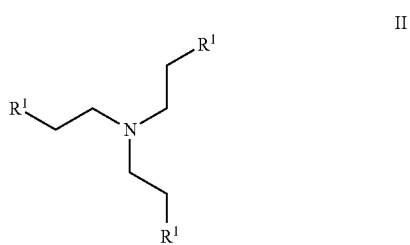

and each $R^1$ is independently —NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, —NH—FK—Z, —NH—RWW—Z, —NH—RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z; and Z is H or Ac.

8. A method for treating a disease or condition associated with infection by a gram positive or gram negative bacteria which comprises administering to a patient in need of such treatment a therapeutically effective amount of the pharmaceutical composition of claim 1.

9. The pharmaceutical composition according to claim 1, wherein the peptide is N[—CH$_2$—CH$_2$—NH—WR—H]$_3$, N[—CH$_2$—CH$_2$—NH—WK—H]$_3$; [H—RW—NH—CH$_2$—CH$_2$—CH$_2$]$_2$N—CH$_2$—CH$_2$—CH$_2$—CH$_2$—N[—CH$_2$—CH$_2$—CH$_2$—NH—WR—H]$_2$; or [H—WK—NH—CH$_2$—CH$_2$—CH$_2$]$_2$N—CH$_2$—CH$_2$—CH$_2$—CH$_2$—N[—CH$_2$—CH$_2$—CH$_2$—NH—WK—H]$_2$.

10. The pharmaceutical composition according to claim 1, wherein the peptide is POPAM-(WR)$_4$; POPAM-(WK)$_4$; TAEA-(WR)$_3$; TAEA-(WK)$_3$; or (RW)$_{4D}$.

11. The pharmaceutical composition according to claim 5, wherein each $R^1$ is independently —NH—WR—Z, —NH—RW—Z, —NH—RF—Z, —NH—FR—Z, —NH—RY—Z, —NH—YR—Z, —NH—KW—Z, —NH—WK—Z, —NH—KY—Z, —NH—YK—Z, —NH—KF—Z, —NH—FK—Z, —NH—RWW—Z, —NH—RFF—Z, —NH—RYY—Z, —NH—KWW—Z, —NH—KYY—Z, —NH—KFF—Z, —NH—WWR—Z, —NH—FFR—Z, —NH—YYR—Z, —NH—WWK—Z, —NH—YYK—Z, or —NH—FFK—Z; and Z is H or Ac.

12. The method of claim 8, wherein the gram positive bacteria is *Staphylococcus aureus*.

13. The method of claim 12, wherein the *Staphylococcus aureus* is methicillin-resistant *Staphylococcus aureus* (MRSA).

14. The method of claim 8, wherein the gram positive bacteria is *Bacillus subtilis*.

15. The method of claim 8, wherein the gram negative bacteria is *Escherichia coli* (*E. coli*).

16. The method of claim 15, wherein the *E. coli* is *E. coli* D31.

\* \* \* \* \*